US009092965B2

(12) United States Patent
Lyons et al.

(10) Patent No.: US 9,092,965 B2
(45) Date of Patent: Jul. 28, 2015

(54) SYSTEM AND METHOD OF DETECTING SLEEP DISORDERS

(76) Inventors: Christopher Thomas Lyons, Tyngsboro, MA (US); Ellen M. Lyons, Tyngsboro, MA (US); Stephen Thomas Lyons, Hudson, NH (US)

(*) Notice: Subject to any disclaimer, the term of this patent is extended or adjusted under 35 U.S.C. 154(b) by 20 days.

(21) Appl. No.: 13/207,073

(22) Filed: Aug. 10, 2011

(65) Prior Publication Data

US 2012/0041343 A1 Feb. 16, 2012

Related U.S. Application Data

(60) Provisional application No. 61/372,202, filed on Aug. 10, 2010.

(51) Int. Cl.
*A61B 5/08* (2006.01)
*G08B 21/06* (2006.01)
(Continued)

(52) U.S. Cl.
CPC ............... *G08B 21/06* (2013.01); *A61B 5/002* (2013.01); *A61B 5/4818* (2013.01); *A61B 5/6817* (2013.01); *A61B 5/1075* (2013.01); *A61B 2562/0219* (2013.01); *A61B 2562/04* (2013.01)

(58) Field of Classification Search
CPC .... A61B 5/4818; A61B 5/6817; A61B 5/002; A61B 5/1075; A61B 2562/0219; A61B 2562/04; G08B 21/06
USPC ......... 600/587, 595, 323–324, 326, 529–543; 340/500, 573.1, 573.7, 689; 381/328, 381/380; 33/340–341, 512
See application file for complete search history.

(56) References Cited

U.S. PATENT DOCUMENTS 4,580,575 A * 4/1986 Birnbaum et al. ............. 600/484
5,081,447 A * 1/1992 Echols ....................... 340/573.7
(Continued)

FOREIGN PATENT DOCUMENTS

DE 102009039915 A1 3/2011
EP 1671578 A1 6/2006
(Continued)

OTHER PUBLICATIONS

Notification of Transmittal of the International Search Report and the Written Opinion of the International Searching Authority, or the Declaration, International Application Number PCT/US2011/047248, filed on Aug. 10, 2011.

*Primary Examiner* — Rene Towa
(74) *Attorney, Agent, or Firm* — Burns & Levinson LLP; Bruce D. Jobse

(57) ABSTRACT

An apparatus for detecting sleep disorders, such as obstructive sleep apnea, includes a housing insertable into an ear canal of a subject. A sensor disposed within the housing measures a position of the subject's head relative to an axis of gravity. A transducer is responsive to the sensor and is capable of creating a stimulus detectable by the subject under certain conditions. In various embodiments, a controller receives signals corresponding to a pitch angle and a roll angle of the subject's head measured by the sensor, determines if the pitch and roll angles correspond to a sleep apnea inducing position, and causes the transducer to generate a stimulus upon determining that the subject's head is in the sleep apnea inducing position more than a predetermined threshold number of times. Various parameters of the stimulus may be modified with successive stimulus generation until a non-sleep apnea inducing position is detected.

10 Claims, 21 Drawing Sheets

(51) Int. Cl.
 *A61B 5/00* (2006.01)
 *A61B 5/107* (2006.01)

(56) References Cited

U.S. PATENT DOCUMENTS

| | | | |
|---|---|---|---|
| 6,095,991 A * | 8/2000 | Krausman et al. | 600/595 |
| 6,920,229 B2 * | 7/2005 | Boesen | 381/380 |
| 7,766,841 B2 * | 8/2010 | Yamamoto et al. | 600/534 |
| 2005/0113646 A1 * | 5/2005 | Sotos et al. | 600/300 |
| 2006/0173257 A1 * | 8/2006 | Nagai et al. | 600/323 |
| 2007/0112287 A1 * | 5/2007 | Fancourt et al. | 600/595 |
| 2007/0208269 A1 * | 9/2007 | Mumford et al. | 600/546 |

FOREIGN PATENT DOCUMENTS

| | | |
|---|---|---|
| GB | 2396043 A | 6/2004 |
| WO | 2007100958 A1 | 9/2007 |

* cited by examiner

SYSTEM AND METHOD OF DETECTING SLEEP DISORDERS

FIELD OF THE INVENTION

This disclosure relates to techniques for detecting sleep disorder conditions, and, more particularly, to a system and method of detecting obstructive sleep apnea.

BACKGROUND OF THE INVENTION

Obstructive sleep apnea (OSA) is the most common category of sleep-disordered breathing. In obstructive sleep apnea, the muscle tone of the body ordinarily relaxes during sleep. At the level of the throat, the human airway is composed of collapsible walls of soft tissue which can obstruct breathing during sleep. In some cases, obstructive sleep apnea requires treatment to prevent low blood oxygen, sleep deprivation, and other complications.

Some techniques to address sleep apnea involve sleeping at a 30-degree or higher elevation of the upper body, as if sleeping in a recliner. Doing so helps prevent the airway from being blocked or obstructed. Furthermore, lateral positions (sleeping on a side), as opposed to supine positions (sleeping on the back), are also recommended as a treatment for sleep apnea. Other treatments include the use of continuous positive airway pressure (CPAP) or oral appliances to keep the airway open during sleep.

Accordingly, there is a need for a sleep apnea detection apparatus that may alert the user when the user's head is positioned in the sleep apnea inducing position.

SUMMARY OF THE INVENTION

Disclosed are technologies for detecting sleep apnea. According to embodiments of the disclosure, a sleep apnea detection apparatus is configured such that when the subject positions himself or herself in a sleep apnea inducing position, the sleep apnea detection apparatus may alert the subject by generating a stimulus, such as an audible alarm. In this way, the subject may adjust his or her position so that the subject is no longer in the sleep apnea inducing position. A sleep apnea inducing position may be any position assumed by the subject that causes the subject to be prone to experiencing sleep apnea. It should be understood that even if a subject is positioned in a sleep apnea inducing position, the subject may not experience sleep apnea. Generally speaking, obstructive sleep apnea occurs when the airway is obstructed or blocked to an extent that a user experiences sleep apnea. The obstruction may be caused by the mass of the tongue or loosened muscles around the throat. Regardless of what causes the obstruction, it has been determined that the position of a subject's head relative to an axis of gravity is related to the occurrence of obstructive sleep apnea. By way of the present disclosure, a subject may be alerted when the subject assumes a sleep apnea inducing position by monitoring the position of the subject's head using a sleep apnea detection apparatus that includes a dual-axis inclinometer.

According to one aspect of the disclosure, a device for detecting sleep disorders includes a housing that can be inserted into an ear canal of a subject. A sensor disposed within the housing measures a position of the subject's head relative to an axis of gravity, while a transducer that is responsive to the sensor, is capable of creating a stimulus detectable by the subject. In various embodiments, a controller may receive signals corresponding to a pitch angle and a roll angle formed between an axis of the subject's head and the axis of gravity as measured by the sensor, determine if the pitch and roll angles correspond to a sleep apnea inducing position, and cause the transducer to generate a stimulus if the subject's head is in the sleep apnea inducing position.

According to another aspect of the disclosure, a method for detecting sleep disorders includes providing a sensor that can be inserted into the ear canal of a subject and measuring the position of the subject's head relative to gravity. Based on the measured position of the subject's head, a determination is made as to whether the subject's head is in a sleep apnea inducing position. If the subject's head is determined to be in the sleep apnea inducing position, the subject may be alerted.

DETAILED DESCRIPTION

The present disclosure will be more completely understood through the following description, which should be read in conjunction with the attached drawings. In this description, like numbers refer to similar elements within various embodiments of the present disclosure. The skilled artisan will readily appreciate that the methods and systems described herein are merely exemplary and that variations can be made without departing from the spirit and scope of the disclosure.

Figure 1:
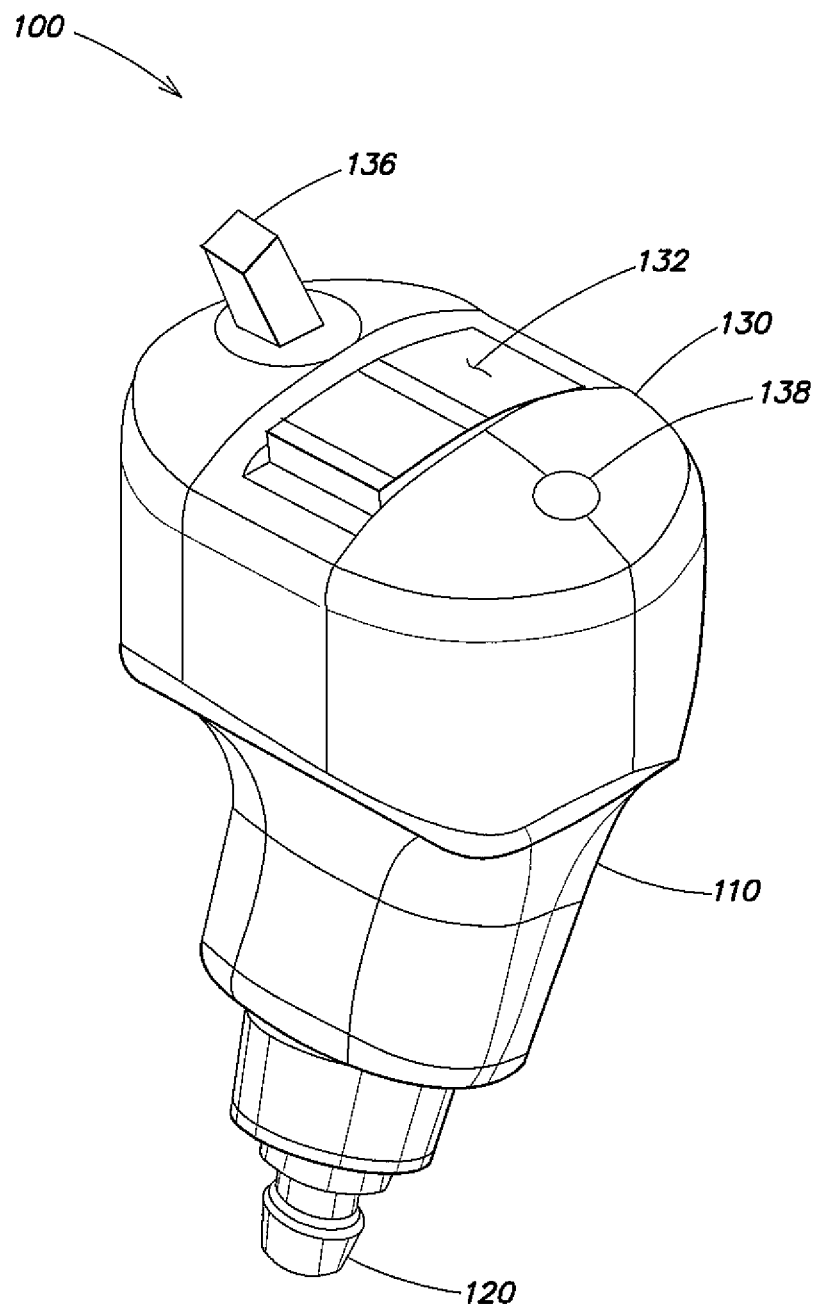
FIG. 1 illustrates a perspective view of an sleep apnea detection apparatus, in accordance with some embodiments of the present disclosure.

Referring now to the figures, FIG. 1 illustrates a perspective view of a sleep apnea detection apparatus 100 in accordance with some embodiments of the present disclosure. The sleep apnea detection apparatus 100 may include a housing 110 having an ear insertion end 120 and an apparatus access end 130. The housing 110 is shaped so that the ear insertion end 120 of the apparatus 100 can be at least partially inserted into the ear canal of a subject. Further, the housing 110 may be made from any of a wide range of materials that may be rigid, semi-rigid, or flexible, such that when the apparatus 100 fits comfortably into the ear canal of subjects. The ear insertion end 120 may be sized such that an optimal protective cover (not shown) may surround a portion of the ear insertion end 120. The protective cover may be made of a material that adjusts in size to ensure that the sleep apnea detection apparatus 100 is snugly fit within the ear canal of the subject. In one embodiment, the protective cover may be made from COMPLY® foam tips, commercially available from the website http://www.complyfoam.com. It should be appreciated that the protective cover may be removed for disposal, replaceable or washable to reduce the risk of an ear infection. However, the sleep apnea detection apparatus 100 may still be operable without the use of the protective cover.

The apparatus access end 130 of the apparatus 100 provides access to an interior chamber defined within the housing 110. In various embodiments, the apparatus access end 130 may be configured to receive a sleep apnea detection circuit 200 that is configured to detect whether the subject wearing the sleep apnea detection apparatus 100 is in a sleep apnea inducing position. Additional details regarding the sleep apnea detection circuit 200 are provided with respect to FIG. 2.

The apparatus access end 130 may include an at least partially movable or removable cover 132 in which a power source 134, such as a battery, a cell, or any other electrical power storage component may be placed. It should be appreciated that the power source 134 (shown in FIG. 2) may be rechargeable and/or removable. In addition, the sleep apnea detection apparatus 100 includes a switch 136 that controls the power being supplied to various components of the sleep apnea detection circuit 200 from the power source 134.

The apparatus access end 130 may also include a rotational component 138 that may be configured to rotate the sleep apnea detection circuit 200 within the interior chamber of the housing 110 in at least two planes. The rotational component 138 may include one or more accessible set screws which may be rotated to adjust the orientation of the sleep apnea detection circuit 200 with respect to the housing 110. The ability to adjust the orientation of the sleep apnea detection circuit 200 enables the circuit to be reoriented as the size, shape, and structure of ear canals of various subjects may vary. Additional details regarding the calibration of the sleep apnea detection apparatus 100 with respect to a particular subject are provided below with respect to the FIGS. 11 and 12.

Although various embodiments of the present disclosure disclose a sleep apnea detection apparatus 100 that is designed to be disposed within an ear canal of a subject, the scope of the present disclosure is not limited to such embodiments. Rather, in some embodiments, the sleep apnea detection apparatus may be configured so as to be placed anywhere on the subject's head so as to detect various head positions relative to the rest of the subject's body. For instance, the sleep apnea detection apparatus may be designed to be strapped around the subjects forehead, worn as a peakless cap or hat, or be positioned on the outside of the subject's ear. Other non-limiting examples include a device insertable in the mouth, nose, or attachable to the subject's hair, amongst others.

Figure 2A:
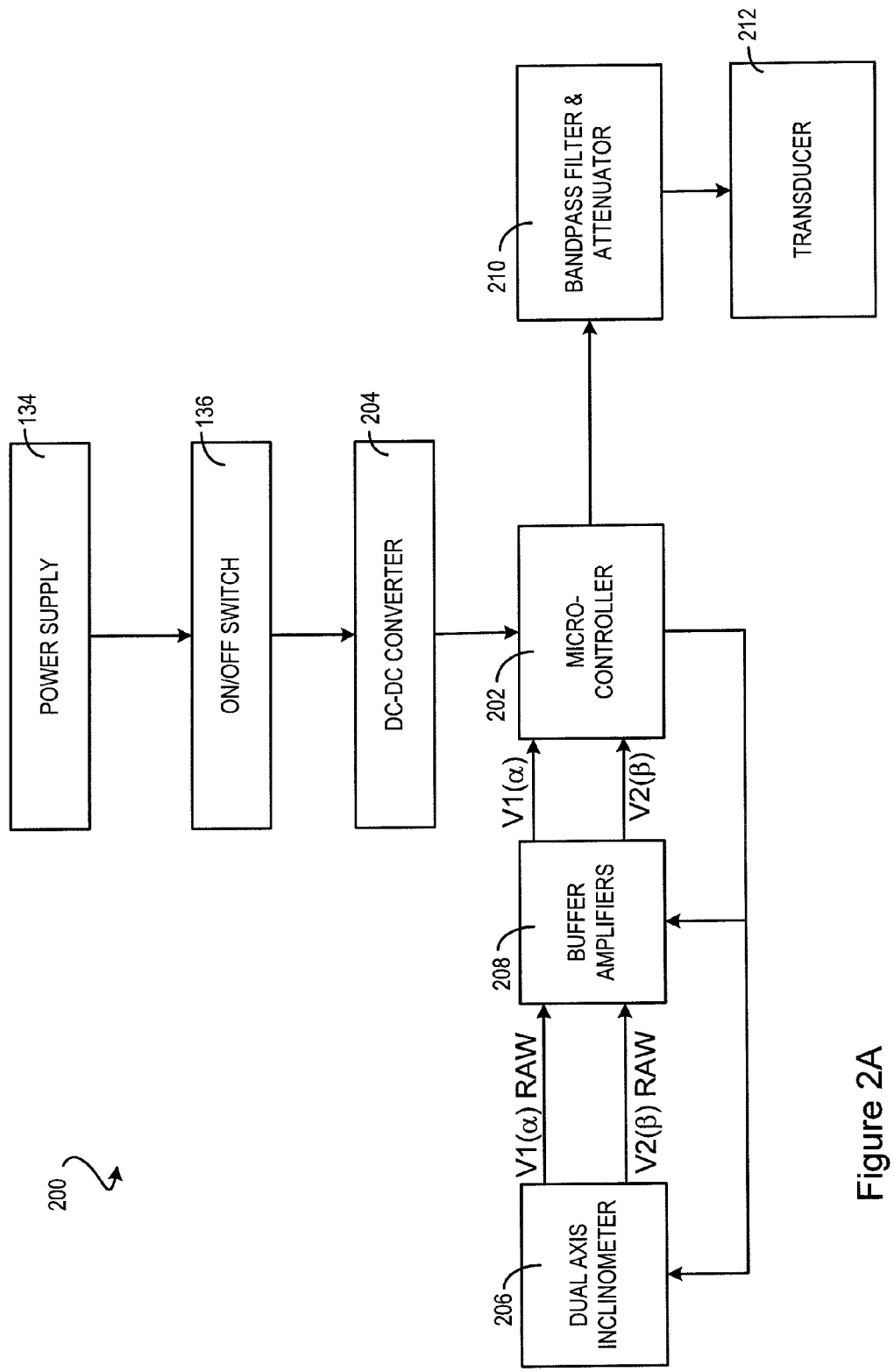
FIG. 2A illustrates a block diagram of a sleep apnea detection circuit in accordance with some embodiments of the present disclosure.
Figure 2B:
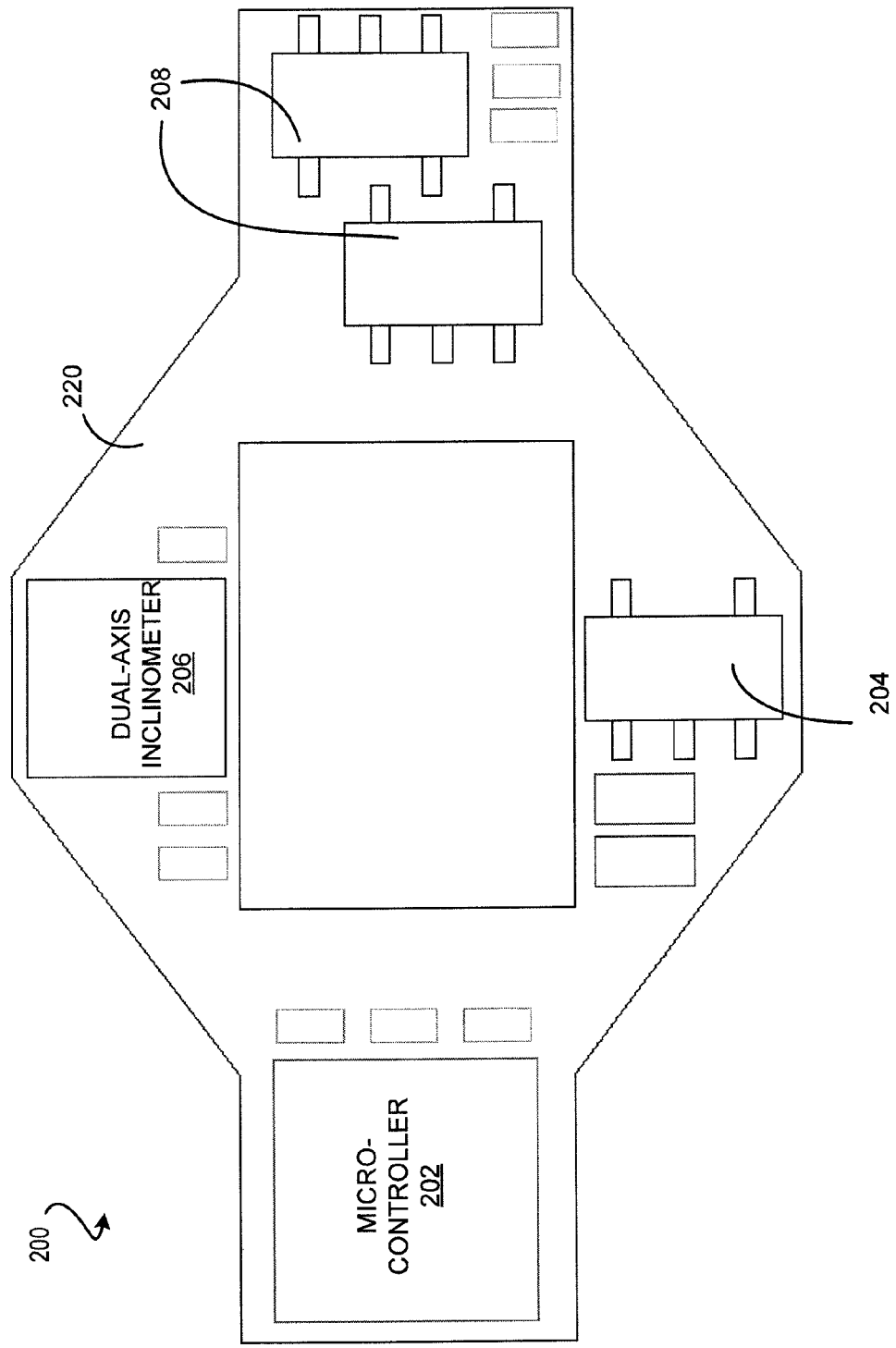
FIG. 2B illustrates a top view of the sleep apnea detection circuit on a circuit board in accordance with some embodiments of the present disclosure.

FIG. 2A illustrates a block diagram of an exemplary sleep apnea detection circuit 200 in accordance with some embodiments. As described above, the sleep apnea detection circuit 200 may be positioned within the interior chamber of the housing 110. It should be appreciated that the sleep apnea detection circuit 200 may be packaged as a single IC package that may be inserted in the interior chamber of the housing 110. FIG. 2B illustrates a top view of the sleep apnea detection circuit 200 on a circuit board 220 in accordance with some embodiments of the present disclosure. Referring now to FIGS. 2A and 2B, the sleep apnea detection circuit 200 may include a microcontroller 202 that is configured to receive power from a DC-DC converter 204. The DC-DC converter 204 may be configured to receive power from the power source 136 and convert the voltage provided by the power source 136 to a voltage suitable for the microcontroller 202. The microcontroller 202 may be electrically coupled to a sensor, including but not limited to a gravitational sensor, such as a three axis inclinometer, a dual-axis inclinometer 206 or a single-axis inclinometer, and one or more buffer amplifiers 208, such that the microcontroller 202 may be able to supply power to the dual-axis inclinometer 206 and the buffer amplifiers 208. The dual-axis inclinometer 206 may be configured to output a first signal corresponding to a measured pitch angle and a second signal corresponding to a measured roll angle. In addition, the microcontroller 202 may be able to receive the first and second signals generated by the dual-axis inclinometer 206. In various embodiments, the dual-axis inclinometer 206 may be coupled to the buffer amplifiers 208, such that the signals generated by the dual-axis inclinometer 206 may be amplified by the buffer amplifiers 208 and provided to the microcontroller 202 as input signals.

The microcontroller 202 may be configured to execute one or more algorithms directed towards calibrating the sleep apnea detection apparatus 100, as well as algorithms for determining whether a subject's head is positioned in a sleep apnea inducing position, and generating a stimulus upon determining that the subject's head is in a sleep apnea inducing position.

The microcontroller 202 may also be configured to provide an output signal that may generate a stimulus indicating that the subject's head is in a sleep apnea inducing position. In one embodiment, the microcontroller 202 may provide an output signal to a bandpass filter and attenuator 210, which passes the output signal to a transducer 212. In various embodiments the transducer 212 may be speaker, a tone generator, a vibration generator, or any other stimulus generating component. It should be appreciated that the transducer 212 may be capable of generating haptic stimulus and/or audible stimulus that is detectable by the subject.

In one embodiment, microcontroller 202 may be implemented as a 16 PIN QFN 4*4*0.9 mm BIT CMOS microcontroller having a part number PIC16F684-1/ML commercially available from Microchip Technology, Inc, Chandler, Ariz. The tri-axis accelerometer used as a dual-axis inclinometer 206 may be implemented with a model KXTC9 accelerometer commercially available from KIONIX®, Ithaca, N.Y. It should be appreciated that various other electrical components, including but not limited to, capacitors, inductors, resistors, and potentiometers may be included as part of the sleep apnea detection circuit 200. In particular, a potentiometer may be coupled to the receiver 212 to adjust the amplitude of the signal being generated. Additionally, or alternatively, the amplitude of the signal can be adjusted using other electrical components or through the microcontroller 202 itself.

The dual-axis inclinometer 206 can generate signals that are indicative of the inclinometer's orientation relative to relative to gravity. Typically, a dual-axis inclinometer is capable of sensing angular position in two directions relative to the direction of the gravitational force. In utilizing a dual-axis inclinometer to detect whether a subject's head is in a sleep apnea inducing position, the sleep apnea detection apparatus 100 may be configured to measure the angular position of the subject's head relative to one or more orthogonal axes. In various embodiments, the inclinometer 206 utilizes an axis representing the instantaneous direction of gravity, referred to hereinafter generally as gravity axis, as one of the orthogonal axes.

As described above, the dual-axis inclinometer 206 may output a first signal corresponding to a pitch angle and a second signal corresponding to a roll angle. The microcontroller 202 may be configured to compare the first signal with threshold values that correspond to a predetermined range of pitch angles that may induce sleep apnea. This predetermined range of pitch angles is referred to as sleep apnea inducing pitch angles. The microcontroller 202 may also be configured to compare the second signal with threshold values that correspond to a predetermined range of roll angles that may induce sleep apnea. This predetermined range of roll angles is referred to as sleep apnea inducing roll angles. In typical embodiments, a subject can experience sleep apnea when the first signal corresponds to a pitch angle that lies within the sleep apnea inducing pitch angles, and the second signal corresponds to a roll angle that lies within the sleep apnea inducing roll angles.

If both the pitch angle and roll angle formed between the subject's head and the corresponding reference axis lie within sleep apnea inducing pitch angles and sleep apnea inducing roll angles, respectively, the microcontroller 202 may generate an output signal that causes the transducer 212 to generate a stimulus that is detectable by the subject. Additional details regarding the sleep apnea inducing pitch angles will be provided with respect to FIGS. 4-6 and sleep apnea inducing roll angles will be provided with respect to FIGS. 7-9.

Although the present disclosure describes embodiments of a sleep apnea detection apparatus that does not record data, it should be appreciated that the apparatus may be configured to do so. In some embodiments, the sleep apnea detection apparatus 100 may be designed for various applications, such as conducting sleep analysis studies, remotely monitoring a subject sleep, and the like. As such, sleep clinics may use the sleep apnea detection apparatus to analyze the various head positions in which a subject may fall asleep, as well as determine the subject's head positions in which the subject experiences sleep apnea. As such, there may be a desire to record the data generated by the dual-axis inclinometer 206 while a subject is asleep.

Figure 2C:
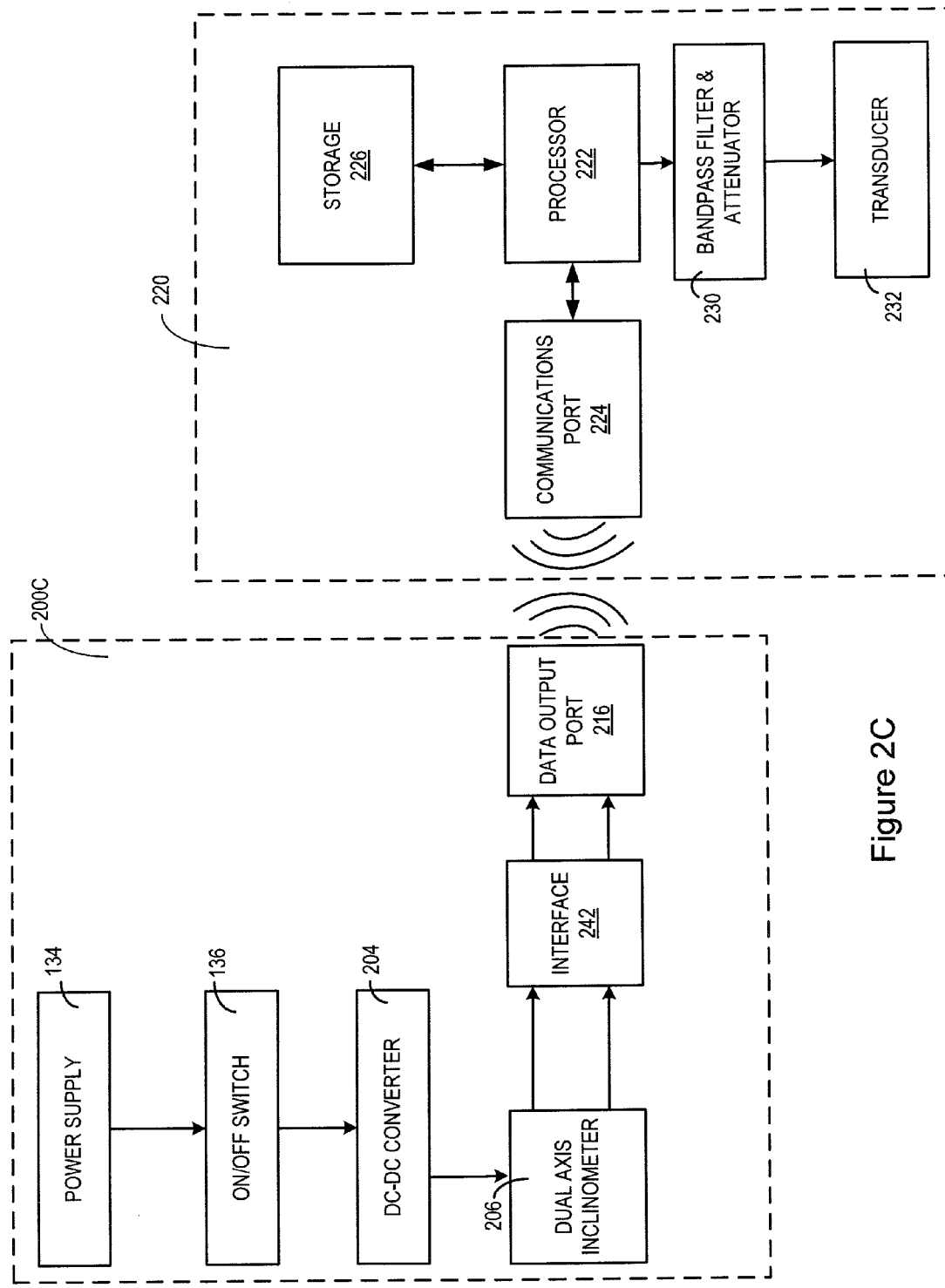
FIGS. 2C-D illustrate block diagrams of sleep apnea detection systems in accordance with embodiments of the present disclosure.

Referring now to FIG. 2C, a sleep apnea detection system may include a local sleep apnea detection circuit 200C that resides in the housing 110. The local sleep apnea detection circuit 200C is similar to the sleep apnea detection circuit 200, but differs in that there is no microcontroller 202. Instead, the local sleep apnea detection circuit 200C includes an interface 242 that allows a data output port 216 to receive the output signals generated by the dual-axis inclinometer and send the information associated with the output signals to a remote sleep apnea processing unit 220. The remote sleep apnea processing unit 220 may include a communications port 224 communicatively coupled to the data output port 216. In addition, the remote sleep apnea processing unit may include a processor 222 that can process the signals received from the local sleep apnea detection circuit 200C and store associated data in a storage location, such as storage 226. In addition, the remote sleep apnea processing unit 220 may provide the output signal to a bandpass filter and attenuator 230, which passes the output signal to a transducer 232, which is capable of alerting the subject.

Figure 2D:
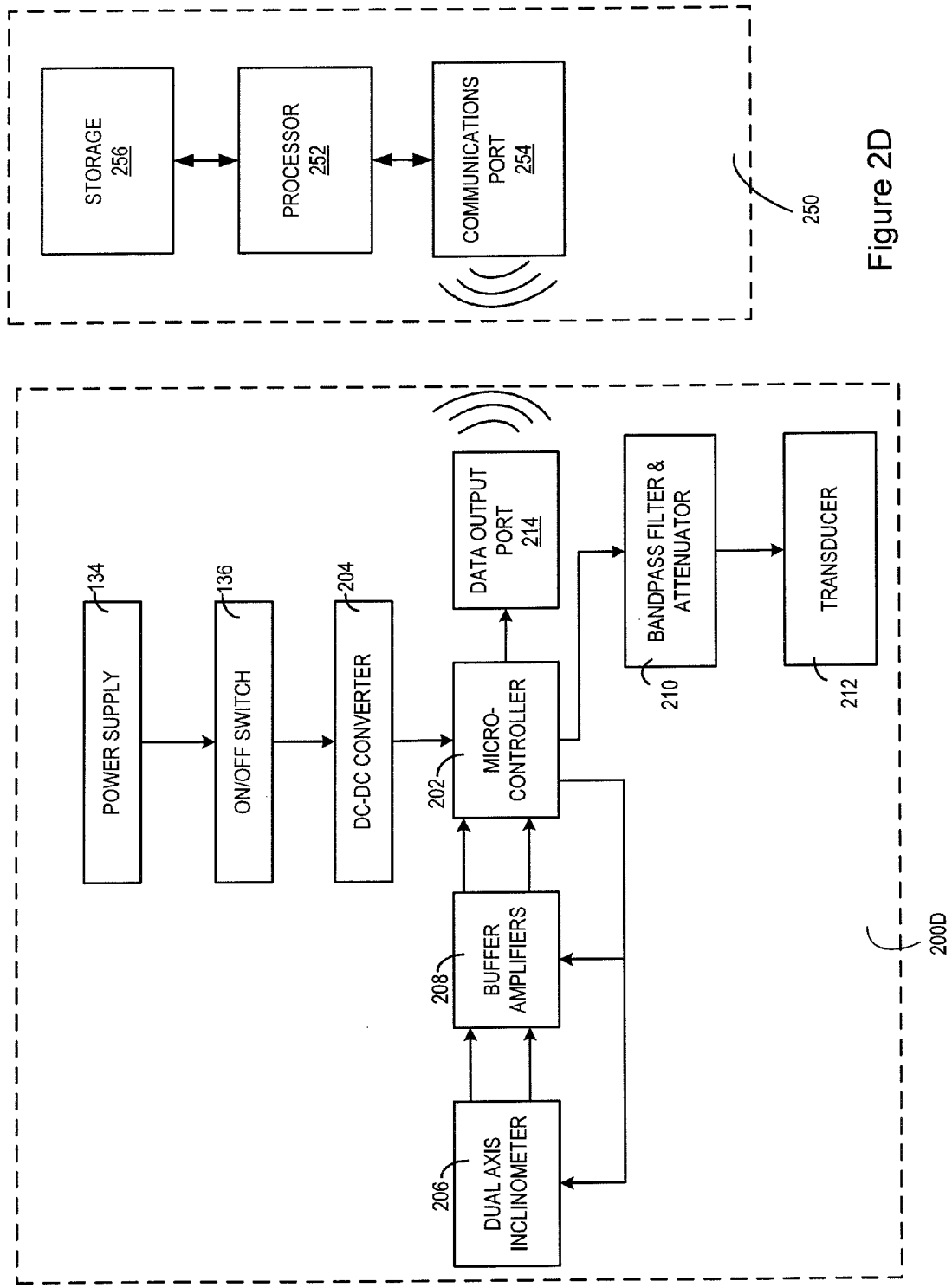

Referring now to FIG. 2D, a sleep apnea detection system may include a local sleep apnea detection circuit 200D that resides in the housing 110. The local sleep apnea detection circuit 200D is similar to the sleep apnea detection circuit 200, but differs in that the microcontroller 202 is coupled to a data output port 216, which can provide the output signals generated by the dual-axis inclinometer 206 to a remote sleep apnea processing unit 250. The remote sleep apnea processing unit 250 may include a communications port 254 communicatively coupled to the data output port 256. In addition, the remote sleep apnea processing unit may include a processor 252 that can process the signals received from the local sleep apnea detection circuit 200D and store associated data in a storage location, such as storage 256.

In various embodiments, the sleep apnea detection apparatus 100 may include a data port 214 through which data from the sleep apnea detection circuit 200 can be transferred to an external storage location, including but not limited to, a computer configured to record such data. The data port may be configured for wired data transfer or wireless data transfer, using technologies, including but not limited to, BLUE- TOOTH, short range wireless data transmission, or other forms of data transmission. In some embodiments, the data storage location may be located near the subject, while in other embodiments, the data storage location may be located at a remote location. In some embodiments, the sleep apnea detection apparatus may be configured to access a communications network, such as WiFi, LAN, WAN, or any other communications network through which the data generated by the dual-axis inclinometer 206 can be transferred to the storage location. In various embodiments, the sleep apnea detection circuit may simply be configured to poll the dual-axis inclinometer 206 for readings, and the output signals from the inclinometer 206 may be provided to an external processing system, which can process the data and generate a stimulus that can get the attention of the subject. Utilizing either of the configurations illustrated in FIG. 2C-D, it should be understood that the communications between the sleep apnea detection apparatus and the sleep apnea processing unit may be bi-directional. For example, using any of the above identified communications protocols, the data from inclinometer 206 may be either pushed to or pulled by processor 222. Utilizing the configuration illustrated in FIG. 2D, the signal to initiate transducer 212 may originate from processing unit 220 in response to data transmitted to unit 220 from unit 200C and evaluated by processor 222.

Figure 3B:
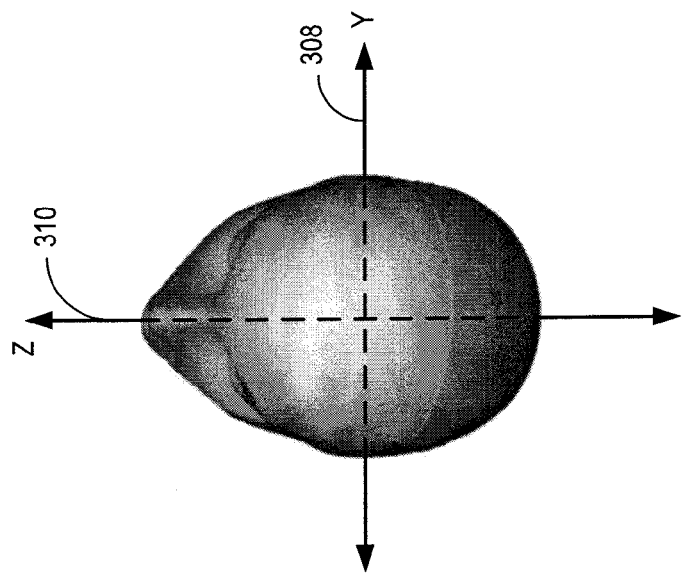
FIGS. 3A and 3B illustrate a hypothetical subject's head and the three orthogonal axes relative to the subject's head in accordance with the present disclosure.
Figure 3A:
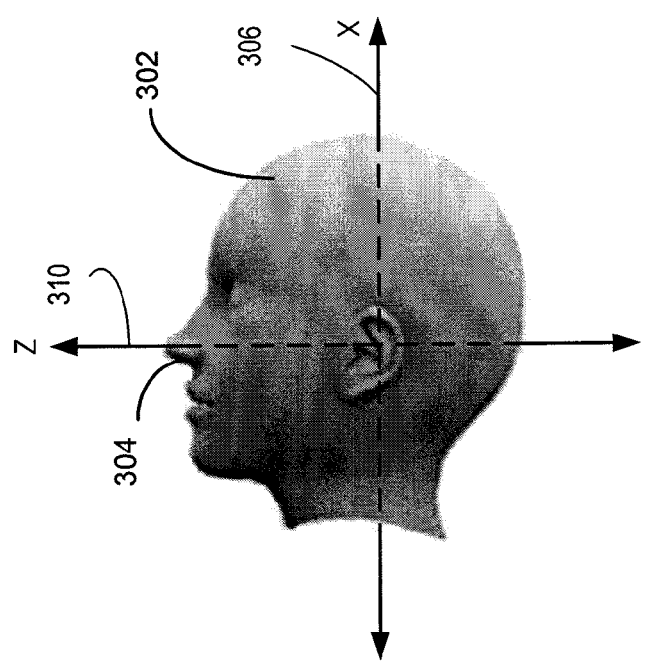
Figure 3C:
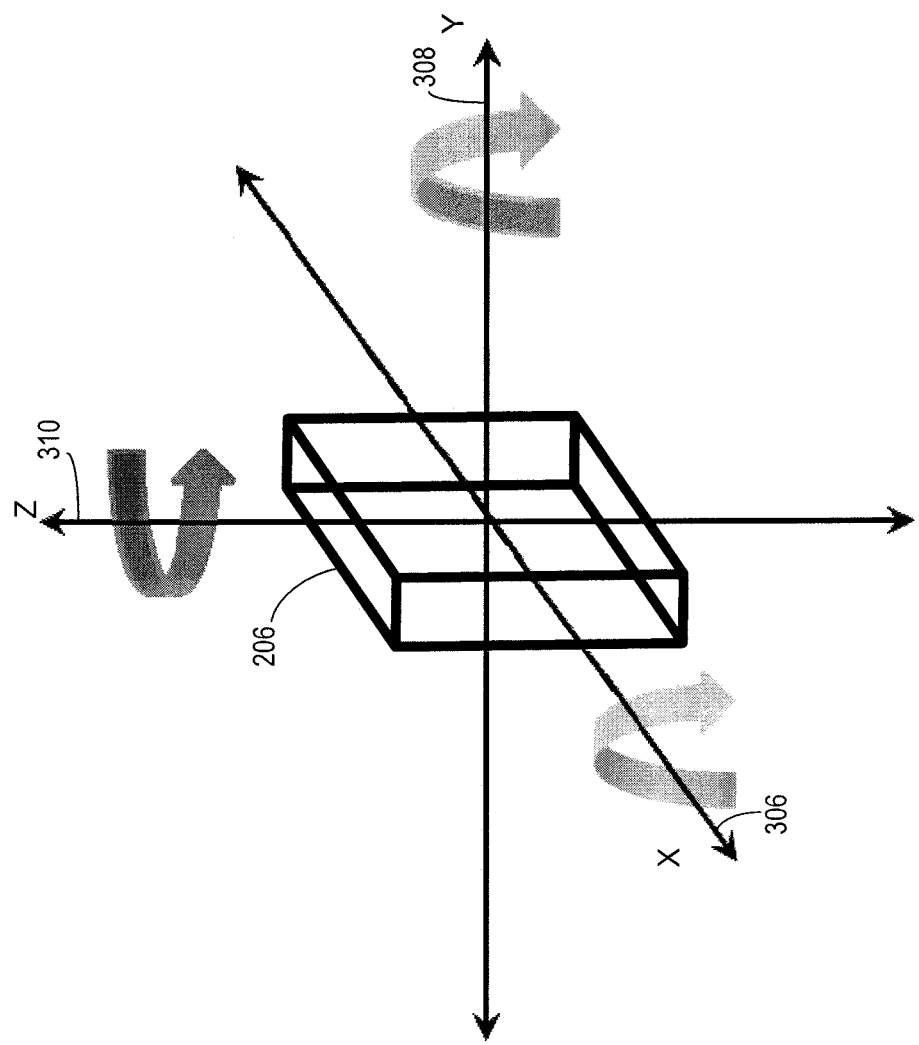
FIG. 3C illustrates the perspective view of a conceptual inclinometer relative to the three orthogonal axes in accordance with embodiments of the present disclosure.

A subject is capable of rotating his or her head 302 about any of three fixed orthogonal axes. For the sake of clarity, FIGS. 3A and 3B illustrate a subject's head 302 and the three fixed orthogonal axes relative to which the subject's head 302 can rotate. Throughout the present disclosure and as shown in FIG. 3A, the three fixed orthogonal axes can be described relative to a hypothetical subject lying in a supine position and looking straight ahead. An x-axis 306 extends from the top of the hypothetical subject's head to the bottom of the hypothetical subject's head such that when the hypothetical subject is standing upright, the x-axis 306 is aligned with an instantaneous axis of gravity. As shown in FIG. 3B, the y-axis 308 refers to an axis that extends from one ear of the hypothetical subject's head to the other ear, and the z-axis 310 refers to an axis that extends from the nose of the hypothetical subject's head 302 to the back of the hypothetical subject's head 302. It should be appreciated that when the hypothetical subject is lying down in the supine position, the z-axis 310 is aligned with the instantaneous direction of gravity.

Rotation of the subject's head 302 about the x-axis 306 is referred to herein as roll, and an angle formed between an axis extending from the nose 304 of the subject's head 302 to the back of the subject's head 302 and the y-axis 308 is referred to herein as the roll angle. Rotation of the subject's head 302 about the y-axis 308 is referred to herein as pitch, and an angle formed between an axis extending from the nose of the subject's head 302 to the back of the subject's head 302 and the z-axis 310 is referred to herein as the pitch angle. Rotation of the subject's head 302 about the z-axis 310 is referred to herein as yaw, and an angle formed between an axis extending from the top of the subject's head 302 to the bottom of the subject's head 302 and the x-axis 306 is referred to herein as the yaw angle. It should be appreciated that any of the axes 306, 308, 310 may or may not be aligned with the axis of gravity. In embodiments, where none of the axes 306, 308, 310 are aligned with the axis of gravity, corrective adjustments can be made in the sleep apnea detection circuit to compensate for the misalignment.

As described above, obstructive sleep apnea is a condition in which pauses in breathing occur during sleep because the airway has become narrowed, blocked, or floppy. During sleep, a subject's muscles become more relaxed, including the muscles that help keep the airway open and allow air to flow into the lungs. Normally, the upper throat still remains open enough during sleep to let air pass. However, some people have a narrower throat area. When the muscles in their upper throat relax during sleep, their breathing can stop for a period of time, oftentimes for more than 10 seconds. The stoppage of breathing is called apnea. It should be appreciated that obstructive sleep apnea can be caused by the tongue forcing the soft palate to obstruct the airway, or by the tongue directly obstructing the airway.

It has been determined that the position of the subject's head 302 relative to the axis of gravity is related to occurrences of obstructive sleep apnea. Positions in which a subject is likely to experience sleep apnea are referred to as sleep apnea inducing positions. A subject is likely to experience sleep apnea when the subject's head 302 is positioned such that a pitch angle formed by an axis of the subject's head 302 and the z-axis 310 that lies within a range of sleep apnea inducing pitch angles and a roll angle formed by an axis of the subject's head 302 and the y-axis 308 that lies within a range of sleep apnea inducing roll angles. The correlation of the position of a subject's head and sleep apnea is tied to the effect gravitational forces have in causing the tongue 324 and/or the soft palate 322 to obstruct the airway 320. In particular, the direction in which gravity exerts a force on the tongue 324 and the soft palate 322 dictates the occurrence of the airway being obstructed. Even though the overall magnitude of gravitational force is constant under gravity, the magnitude of the gravitational force that causes the tongue 324 and the soft palate 322 to obstruct the airway 320 changes as the position of the subject's head changes. Accordingly, certain head positions are more likely than others to cause an occurrence of obstructive sleep apnea.

Typically, when the subject is in a supine position and looking straight ahead along the z-axis 310, the gravitational forces acting on the tongue 324 and the soft palate 322 that can cause the airway 320 to be obstructed are at a maximum. The relationship of the airway crush force and the pitch angle $\Theta_p$ can be given by Equation 1 below $$F = m*a*\sin(\Theta_p) \quad \text{(Equation 1)}$$

where F is the airway crush force, m is the effective mass of tongue tissue, a is the acceleration due to gravity, and $\Theta_p$ is the pitch angle, which is measured relative to the z-axis 310. Similarly, the relationship of the airway crush force and the roll angle $\Theta_r$ can be given by Equation 2 below:

$$F = m*a*\sin(\Theta_r) \quad \text{(Equation 2)}$$

where F is the airway crush force, m is the effective mass of tongue tissue, a is the acceleration due to gravity, $\Theta_r$ is the roll angle, which is measured relative to the y-axis 308.

Figure 4B:
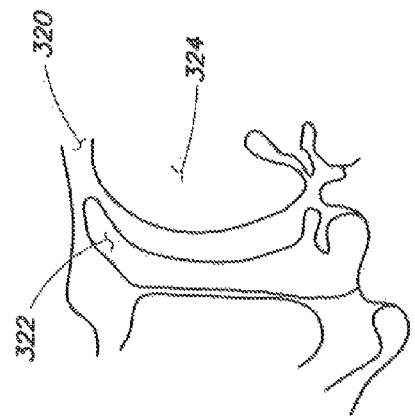
FIGS. 4A-D illustrate a hypothetical subject's head oriented at various pitch angles and a corresponding gravitational force acting on the subject's airway in accordance with embodiments of the present disclosure.
Figure 4D:
Figure 4A:
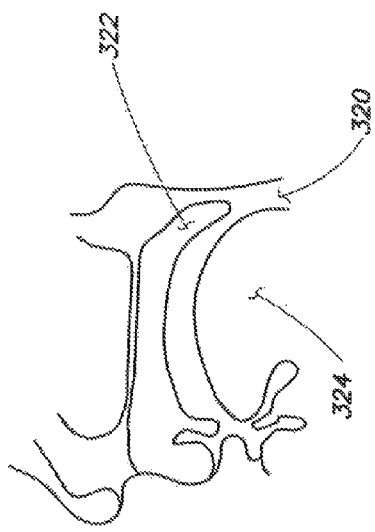
Figure 4C:
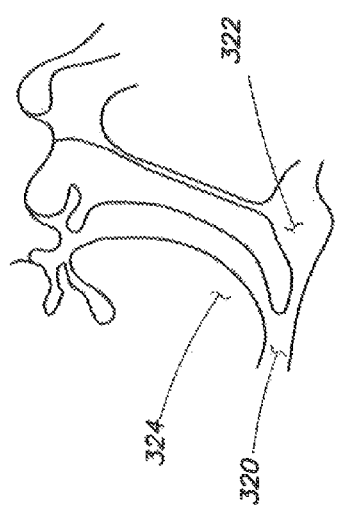

FIGS. 4A-D illustrate a subject's head oriented at various pitch angles and a corresponding gravitational force acting on the subject's airway in accordance with some embodiments of the present disclosure. In particular, FIG. 4A illustrates the subject's head 302 in a supine position such that the pitch angle $\Theta_p$ formed between an axis extending from the top of the subject's head to the bottom of the subject's head 302 and the z-axis 310 is 90°. When the pitch angle $\Theta_p$ is 90°, the airway crush force is at a maximum. FIG. 4B illustrates the subject's head 302 in an upright position, such that the pitch angle $\Theta_p$ formed between an axis extending from the top of the subject's head to the bottom of the subject's head 302 and the z-axis 310 is 180°. When the pitch angle $\Theta_p$ is 180°, the airway crush force is at a minimum, as explained by the equation provided above. FIG. 4C shows the subject's head at a pitch angle that lies between 90°<$\Theta_p$<180°, in which case only a portion of the total airway crush force is directed towards forcing the tongue 324 or soft palate 322 to obstruct the airway 320. FIG. 4D shows the subject's head at a pitch angle $\Theta_p=270°$, in which case the gravitational force acts upon the walls 322 of the airway 320 in the opposite direction such that the airway 320 remains open.

Figure 5A:
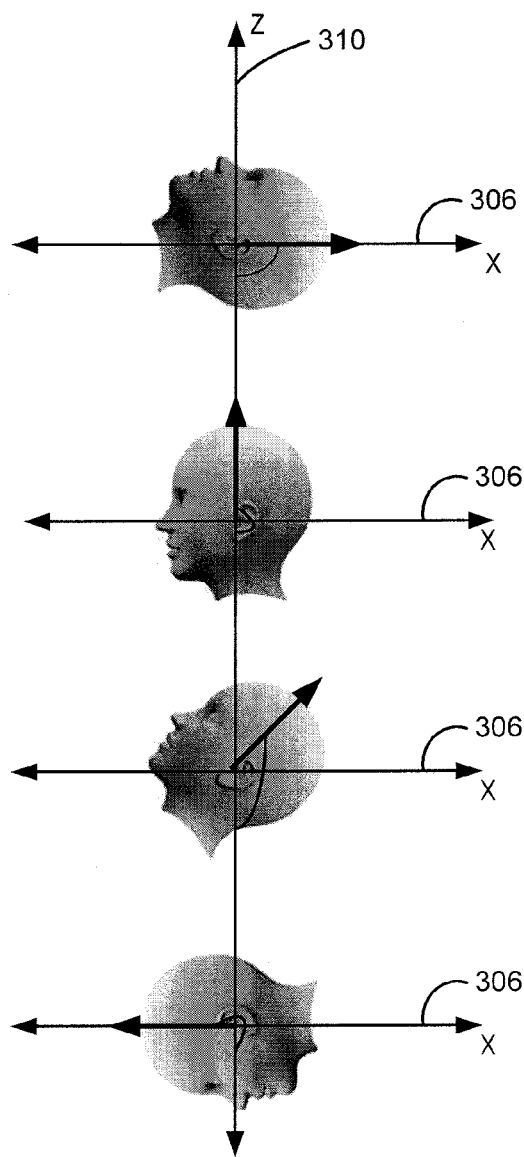
FIG. 5A illustrates a conceptual representation of a hypothetical subject's head oriented at various pitch angles corresponding to the pitch angles of FIG. 4A-D in accordance with embodiments of the present disclosure.
Figure 5B:
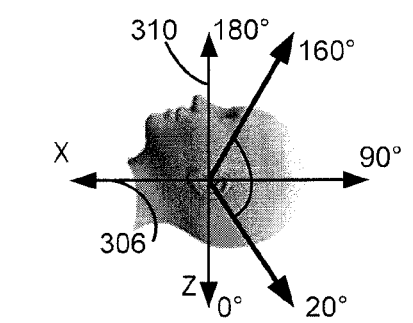
FIG. 5B illustrates a conceptual representation of a hypothetical subject's head and a range of sleep apnea inducing pitch angles in accordance with embodiments of the present disclosure.

FIG. 5A illustrates conceptual views of a subject's head at various pitch angles corresponding to the pitch angles of the subject's head with respect to FIGS. 4A-D. FIG. 5B illustrates a range of sleep apnea inducing pitch angles relative to the z-axis 310. As shown in FIG. 5B, the range of sleep apnea inducing pitch angles may extend from 20° to 160°.

Figure 6:
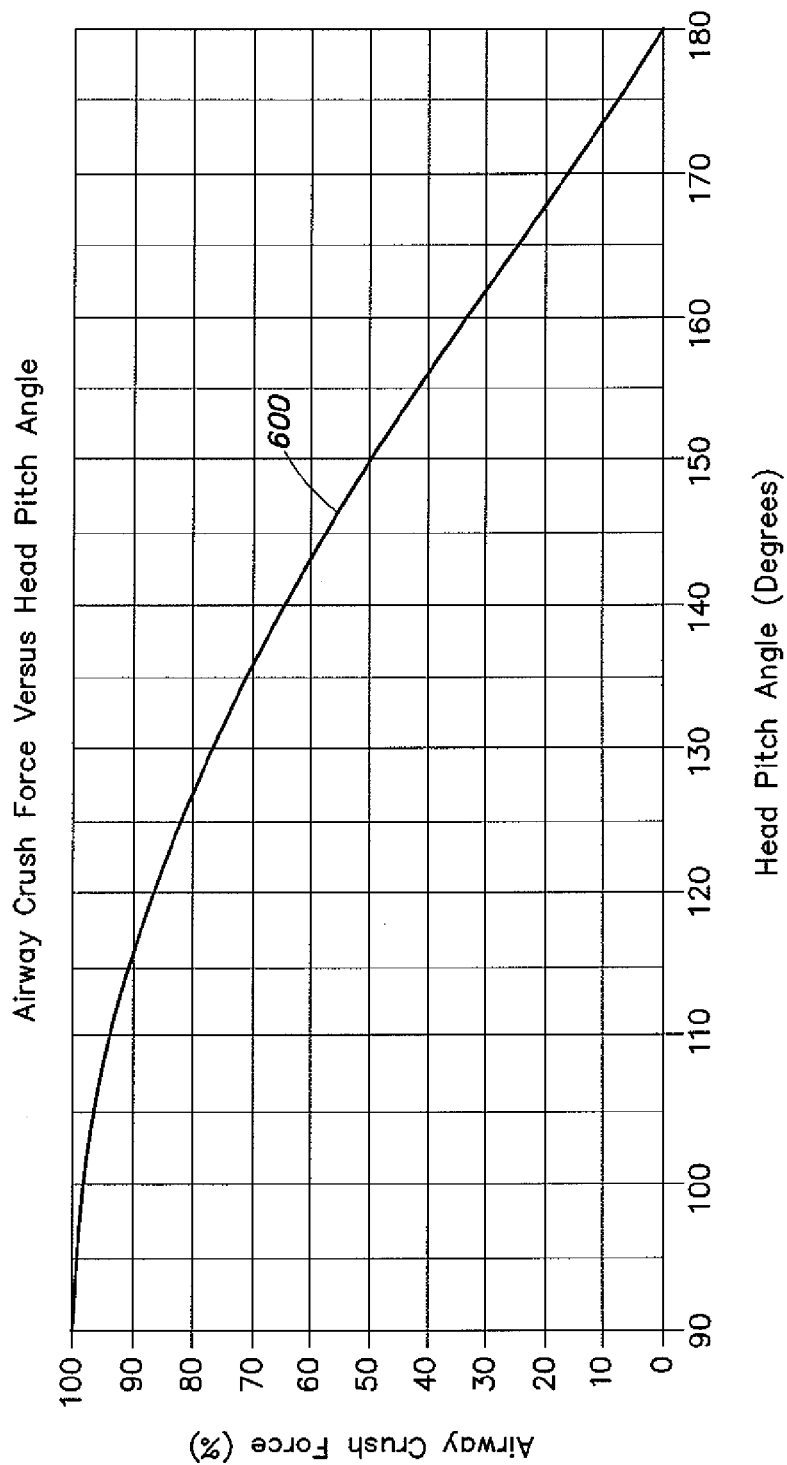
FIG. 6 illustrates a plot of the airway crush force percentage over a range of pitch angles in accordance with embodiments of the present disclosure.

FIG. 6 illustrates a plot of the airway crush force percentage over a range of pitch angles in accordance with some embodiments of the present disclosure. As described above, the relationship of the airway crush force and the pitch angle $\Theta_p$ is given by Equation 1.

As described above with respect to FIGS. 4 and 5, a subject may sleep in a supine position, in which the pitch angle formed by the subject's head is 90°. Although the subject may sleep at pitch angles slightly less than 90°, angles much smaller than 90° may be uncomfortable and undesirable. Accordingly, in some embodiments, a more practical range of sleep apnea inducing pitch angles may be at approximately 75° or greater.

Figure 7:
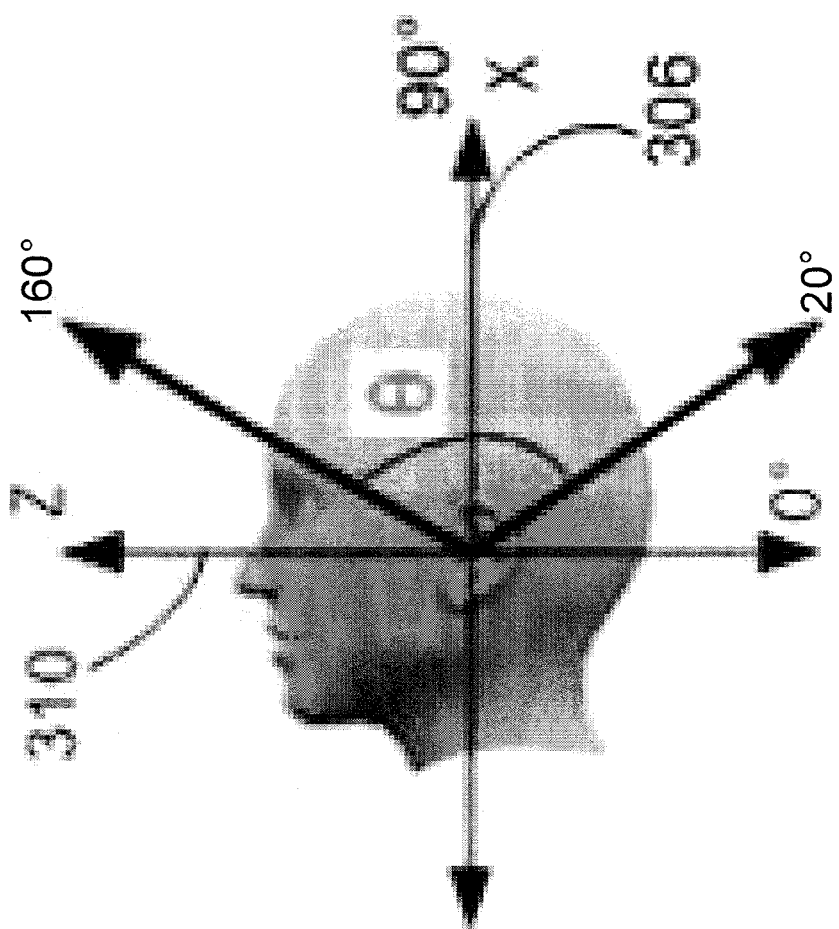
FIG. 7 illustrates a range of pitch angles in which the subject may experience sleep apnea in accordance with embodiments of the present disclosure.

FIG. 7 illustrates a range of pitch angles in which the subject may experience sleep apnea in accordance with some embodiments of the present disclosure. The sleep apnea detection circuit 200 may be configured to generate a stimulus when the pitch angle and the roll angle both lie within a range of sleep apnea inducing pitch angle and roll angle positions, respectively. The range of sleep apnea inducing pitch angles may correspond to angles associated with a threshold percentage of the maximum airway crush force that can be exerted to cause the airway 320 to be obstructed and cause sleep apnea.

It has been determined that sleep apnea may occur when the airway crush force causes the airway to be obstructed by either the tongue 324 or the soft pallet 322. In various embodiments, the threshold percentage at which the airway is obstructed may be 35%, which corresponds to pitch angles that are greater than approximately 20° and less than approximately 160°. In other embodiments, the threshold percentage may be 40%, which corresponds to pitch angles that are greater than approximately 25° and less than approximately 155°. In yet another embodiment, threshold percentage may be 50%, which corresponds to the pitch angles that are greater than approximately 30° and less than approximately 150°. It should be appreciated that as the threshold percentage increases, the likelihood of sleep apnea occurring also increases. Moreover, the range of pitch angles also gets narrower as the threshold percentage increases as well. It should also be appreciated that the angles that define the range do not necessarily have to add up to 180°. Rather, a range of pitch angles that induce sleep apnea may extend from approximately 60° to 150°.

Figure 8A:
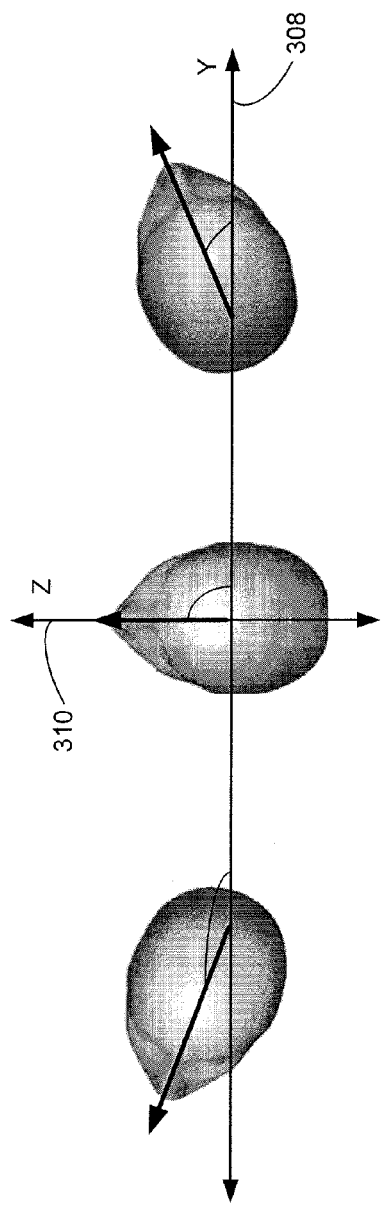
FIG. 8A illustrates conceptual views of a subject's head oriented at various roll angles in accordance with embodiments of the present disclosure.
Figure 8B:
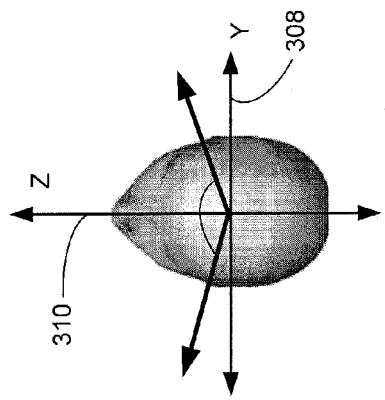
FIG. 8B illustrates a conceptual representation of a subject's head and a range of sleep apnea inducing roll angles in accordance with some embodiments of the present disclosure.

FIG. 8A illustrates conceptual views of a subject's head oriented at various roll angles in accordance with some embodiments of the present disclosure. In particular, FIG. 8A shows the subject's head rotating about the x-axis 306, such that the roll angle $\Theta_r$ relative to the y-axis 308 increases from 0° to 180° as the subject rolls his head from his right side to his left side, or if the subject rolls his head and body from his right side to his left side. As shown in FIG. 8B, a range of sleep apnea inducing roll angles is shown, extending from 25° to 155° relative to the y-axis 308.

Although possible sleep apnea inducing positions may include roll angles that extend from approximately 12° to 168° relative to the y-axis 308, the sleep apnea detection apparatus 100 may be configured such that the sleep apnea detection apparatus 100 considers roll angles that range from approximately 25° to 155° to lie within the range of sleep apnea inducing positions, as indicated in FIG. 8B. This is because a subject, while sleeping, may not be able to maintain the roll angle less than 12° or greater than 168° relative to the y-axis 308. However, by including these ranges of angles within the sleep apnea inducing range, the accuracy of the sleep apnea detection apparatus 100 may be degraded. However, it should be appreciated that in various embodiments, these angles may be included within the range of angles that the sleep apnea detection apparatus 100 considers to lie within the sleep apnea inducing range.

Figure 9:
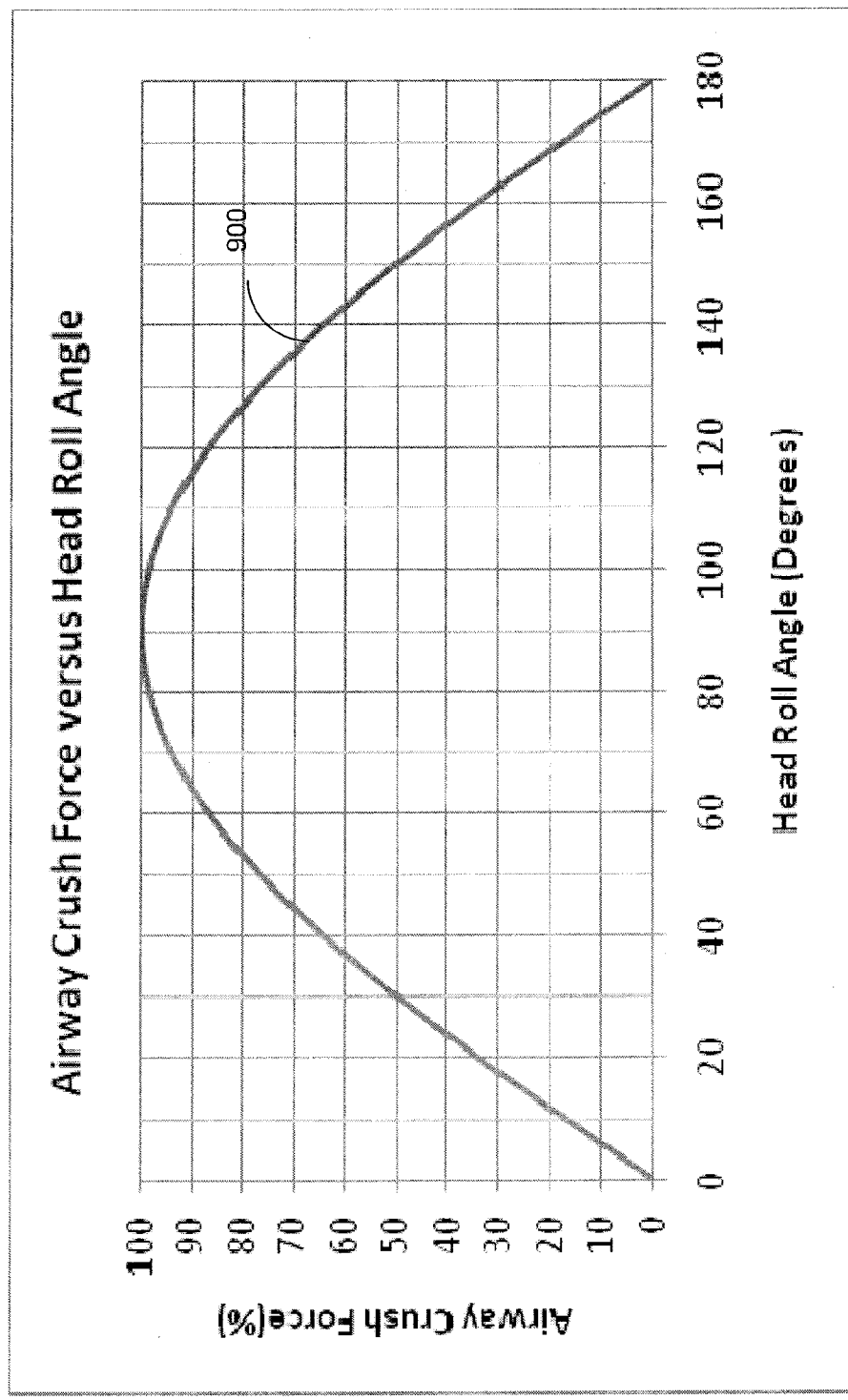
FIG. 9 illustrates a plot of the airway crush force percentage over a range of roll angles in accordance with some embodiments of the present disclosure.

FIG. 9 illustrates a plot of the airway crush force percentage over a range of roll angles in accordance with some embodiments of the present disclosure. As described above, the relationship of the airway crush force and the roll angle $\Theta_r$ is given by Equation 2.

It has been determined that sleep apnea may occur when the airway crush force exceeds a threshold percentage of the airway crush force. In various embodiments, the threshold percentage may be 35%, which corresponds to roll angles that are greater than approximately 20° and less than approximately 160°. In other embodiments, the threshold percentage may be 40%, which corresponds to roll angles that are greater than approximately 25° and less than approximately 155°. It yet another embodiment, threshold percentage may be 50%, which corresponds to the pitch angles that are greater than approximately 30° and less than approximately 150°. It should be appreciated that as the threshold percentage increases, the likelihood of sleep apnea occurring also increases. Moreover, the range of roll angles also gets narrower as the threshold percentage increases as well.

The sleep apnea detection apparatus 100 may not generate a stimulus as long as the subject assumes a position in which the pitch angle $\Theta_p$ does not lie within the pitch angle range of sleep apnea inducing positions or the roll angle $\Theta_r$ does not lie within the roll angle range of sleep apnea inducing positions that are predefined in the sleep apnea detection circuit 200. In one embodiment, pitch angles that does not lie within the pitch angle range of sleep apnea inducing positions include pitch angles that exceed 160° or are less than 20° relative to the z-axis 310. It should be appreciated that even though some angles do not induce sleep apnea, sleeping in such positions may may be undesirable or uncomfortable. For instance, sleeping at pitch angles less than 90° or pitch angles greater than 270° relative to the z-axis 310 may be uncomfortable or undesirable. Similarly, roll angles that does not lie within the roll angle range of sleep apnea inducing positions include roll angles that are less than 20° or exceed 160° relative to the y-axis 308. It should be appreciated that it may not be possible for a typical human to sleep at roll angles that exceed 250° or are less than −70°. However, since the sleep apnea detection apparatus is configured to only determine whether a subject is positioned in a sleep apnea inducing position, no action is taken when the subject's head is positioned at any angle that does not lie within the range of angles that induce sleep apnea.

The sleep apnea detection apparatus 100 can generate a stimulus when the subject assumes a position in which the pitch angle $\Theta_p$ lies within a range of sleep apnea inducing positions, such as pitch angles that lie between approximately 20° and 160° relative to the z-axis 310, and the roll angle $\Theta_r$ is between approximately 20° and 160° relative to the y-axis 308.

Figure 10:
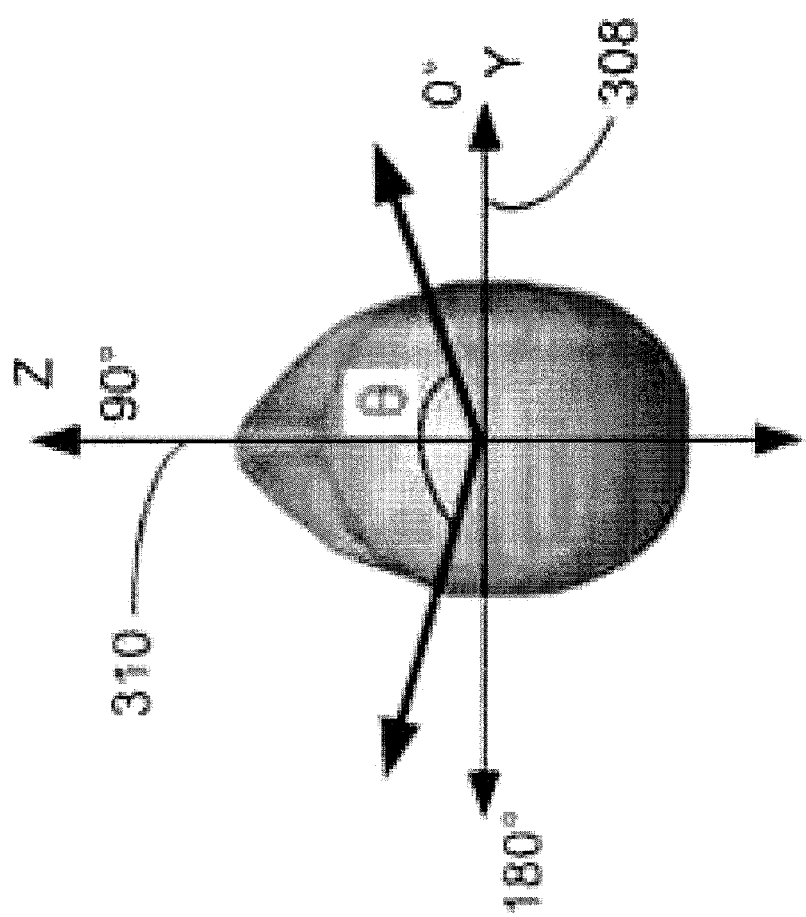
FIG. 10 illustrates a range of roll angles in which the subject may experience sleep apnea in accordance with some embodiments of the present disclosure.

FIG. 10 illustrates a range of roll angles in which the subject may experience sleep apnea in accordance with some embodiments of the present disclosure. As described above, the sleep apnea detection circuit 200 may be configured to generate a stimulus when the pitch angle and the roll angle both lie within a range of sleep apnea inducing pitch angle and roll angle positions respectively. The range of sleep apnea inducing roll angles may correspond to roll angles associated with a threshold percentage of the maximum airway crush force that can be exerted to cause the airway 320 to be obstructed and cause sleep apnea.

It has been determined that sleep apnea may occur when the airway crush force causes the airway to be obstructed by either the tongue 324 or the soft pallet 322. In various embodiments, the threshold percentage at which the airway is obstructed may be 35%, which corresponds to roll angles that are greater than approximately 20° and less than approximately 160°. In other embodiments, the threshold percentage may be 40%, which corresponds to roll angles that are greater than approximately 25° and less than approximately 155°. It yet another embodiment, threshold percentage may be 50%, which corresponds to the roll angles that are greater than approximately 30° and less than approximately 150°. It should be appreciated that as the threshold percentage increases, the likelihood of sleep apnea occurring also increases. Moreover, the range of roll angles also gets narrower as the threshold percentage increases as well. It should also be appreciated that the angles that define the range do not necessarily have to add up to 180°. Rather, a range of roll angles that induce sleep apnea may extend from 60° to 150°.

Although the present disclosure discloses the use of a dual-axis inclinometer 206 to determine the pitch and roll angles of a subject's head, other types of inclinometers, accelerometers, gyroscope or sensors may be utilized to determine the orientation of the subject's head relative to the three fixed axes 306, 308, 310. In various embodiments, a single-axis accelerometer may be utilized. In particular, a single-axis accelerometer is capable of providing angular information related to a first axis, and angular information with reduced sensitivity in a second axis of the other two mutually orthogonal axes. Since the single axis accelerometer is capable of generating different sets of output voltages along two separate axes, a single axis accelerometer may be used as long as the range of pitch angles that define the sleep apnea inducing positions and the range of roll angles that define the sleep apnea inducing positions are the same.

From FIGS. 6 and 9, it can be appreciated that the sleep apnea inducing positions can be defined by pitch angles and roll angles that are the same. For instance, the pitch angle range may be set at $20°<\Theta_p<160°$ and the roll angle range may be set at $20°<\Theta_r<160°$ off of their respective axes. In one embodiment, the sleep apnea inducing pitch angle position may be set at 30° off of the x-axis 306, which may correspond to a threshold output voltage generated by the single-axis accelerometer. As the subject's head moves towards a supine position and rolls his head from $0°<\Theta_r<180°$, the sleep apnea detection circuit may generate a stimulus as the voltage outputted by the single-axis accelerometer reaches the threshold output voltage. Since the threshold output voltage correlates to a roll angle of approximately 30° relative to the y-axis 308 or 150° relative to the y-axis 308, the stimulus can be generated when the roll angle is within the range of sleep apnea inducing positions.

The orientation of the dual-axis inclinometer 206 may be an important consideration for the accurate and consistent functioning of the sleep apnea detection apparatus 100. The dual-axis inclinometer 206 generates output signals indicating the relative orientation of the sleep apnea detection apparatus 100 relative to the three fixed orthogonal axes 306, 308, 310. Since the microcontroller 206 is designed to generate a stimulus when the subject's head 302 assumes a sleep apnea inducing position, it is important to make sure that the dual-axis inclinometer 206 is generating output signals that accurately correspond to the right roll angles and pitch angles. The overall accuracy of the apnea detection apparatus 100 is set by both a rotational error and a planarity error, when placed in the ear.

The rotational error is associated with the pitch angle. In various embodiments, acceptable ranges of the rotational error may include pitch angles that are between 170° and 190° relative to the axis of gravity. The rotational error can be easily removed during calibration as the subject rotates the sleep apnea detection apparatus 100 within the ear canal about the axis of gravity until the pitch angle lies between 170° and 190° relative to the axis of gravity. In various embodiments, during a calibration process, the sleep apnea detection apparatus may generate a stimulus indicating that the sleep apnea detection apparatus is not calibrated. As the apparatus 100 is rotated within the ear canal of the subject, the sleep apnea detection apparatus 100 may generate a different stimulus indicating that the apparatus no longer has a rotational error. In various embodiments, the sleep apnea detection apparatus may be configured to factor the rotational error when determining whether the subject's head 302 lies within in a sleep apnea inducing pitch angle range.

Figure 11A:
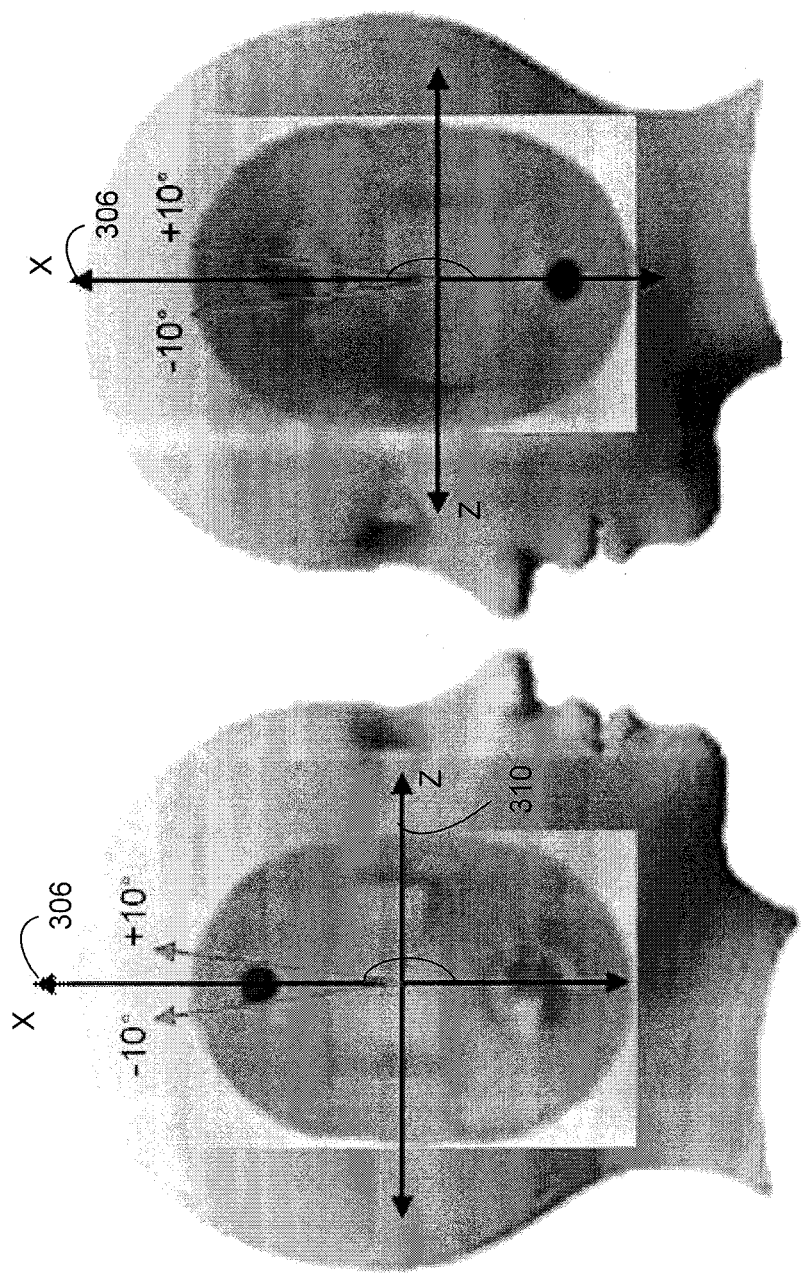
FIG. 11A illustrates side views of a subject's head and respective orientations of the sleep apnea detection apparatus in accordance with some embodiments of the present disclosure.

Referring now to FIG. 11A, side views of a subject's head and respective orientations of the sleep apnea detection apparatus 100 are shown. A subject may assume a sleep apnea inducing position based on the orientation of the subject's head. In particular, the subject may assume a sleep apnea inducing position when the subject's head assumes a position in which the pitch angle lies within the sleep apnea inducing range of pitch angles, and, the roll angle lies within the sleep apnea inducing range of roll angles. As described above, since the sleep apnea detection apparatus 100, which contains the dual-axis inclinometer 206, is at least partially inserted within the ear canal of the subject, pitch and roll movements of the subject's head relative to the fixed orthogonal axes 306, 308 may change the orientation of the dual-axis inclinometer 206 relative to the two fixed orthogonal axes 306, 308. Accordingly, the output signal generated by the dual-axis inclinometer 206 may also change, reflecting changes in the pitch and roll angles.

Prior to first use of the sleep apnea detection apparatus, a calibration process may be performed since the dual-axis inclinometer determines pitch and roll angles relative to gravity or vertical. As such, when the sleep apnea detection circuit 200 including the dual-axis inclinometer 206 is positioned within a subject's ear canal, the dual-axis inclinometer 206 can provide pitch and roll angles relative to the two orthogonal axes. As part of the calibration process, which will be described with respect to FIG. 12, the rotation angle of the dual-axis inclinometer 206 may lie within approximately 170° and 190° relative to the gravity axis 306, as indicated in FIG. 11A. Depending upon whether the subject wears the sleep apnea detection apparatus 100 in their left ear or right ear, the sleep apnea detection circuit 200 positioned within the housing 110 may be rotated 180° relative to the housing 110.

As described above, the overall accuracy of the apnea detection apparatus 100 may also depend on a planarity error. A planarity error arises when the dual-axis inclinometer 206 is not aligned with each of the three orthogonal axes. Aligning the dual-axis inclinometer 206 perpendicular to a line drawn from ear to ear, however is not as easy to calibrate, detect, or adjust, as the planarity error varies based on the shape of the subject's ear canal. Planarity can be detected using a gyroscope, which in itself would require calibration. Because the shape and angle of each individual's ear canal may vary slightly from subject to subject, a one-time planarity adjustment to match the subject's unique ear canal orientation may be required. This one-time adjustment may be performed by the subject or by a doctor by rotating the sleep apnea detection circuit 200 within the housing 110. As described above, the rotational component 138, such as a set screw, accessible from the access end 130 of the sleep apnea detection apparatus 100 can rotate the sleep apnea detection circuit 200 relative to the housing 110. In various embodiments, separate screws may be used to rotate the inclinometer 206, or the sleep apnea detection circuit 200 within the housing 110, about a particular axis.

Figure 11C:
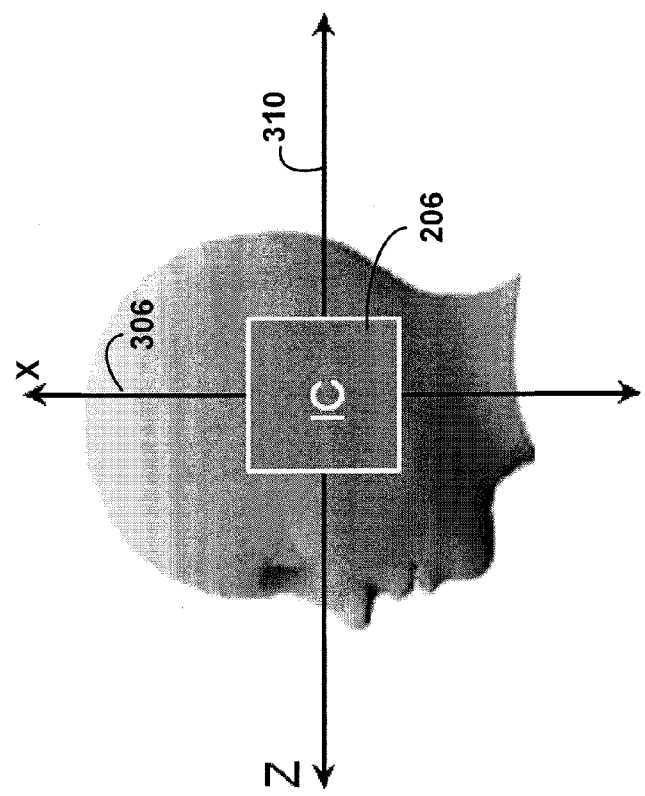
FIGS. 11B-C are front and side views of a subject's head showing the orientation of the dual-axis inclinometer relative to the orthogonal axes in accordance with some embodiments of the present disclosure.
Figure 11B:
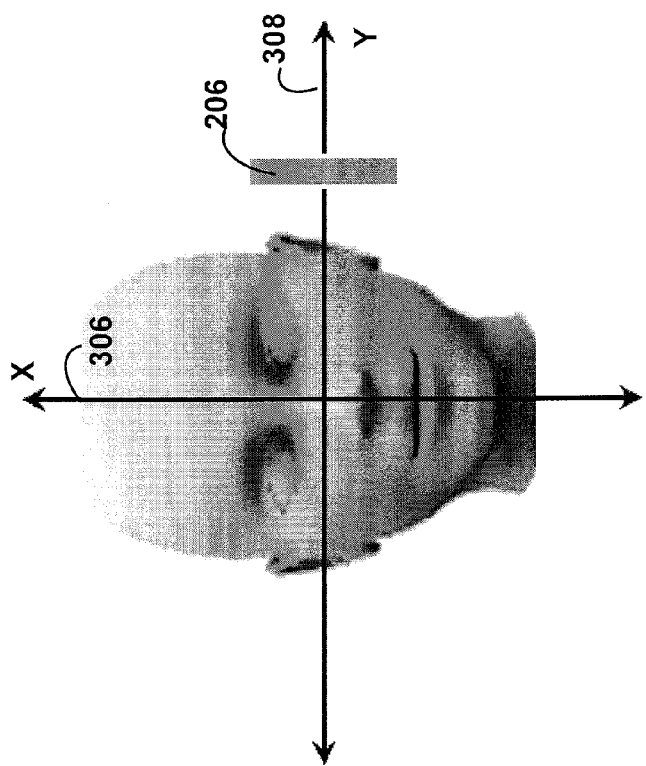

FIGS. 11B-C are front and side views of a subject's head showing the orientation of the dual-axis inclinometer relative to the orthogonal axes in accordance with some embodiments of the present disclosure. By rotating the sleep apnea detection circuit 200 within the housing 110, the orientation of the dual-axis inclinometer 206 also changes. To eliminate planarity errors, the dual-axis inclinometer 206 may be oriented such that the dual-axis inclinometer is aligned with the three fixed orthogonal axes 306, 308, 310.

Figure 12:
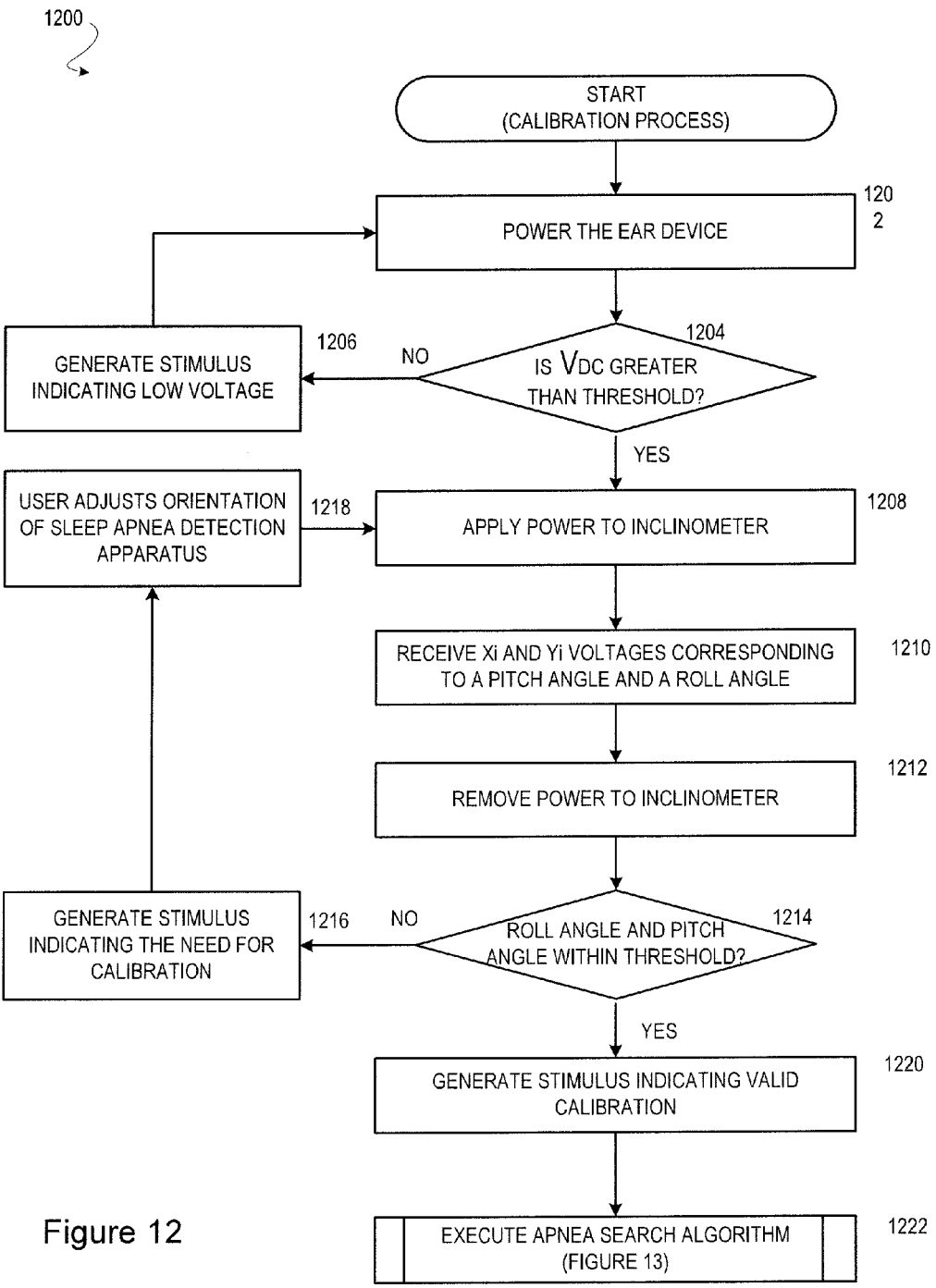
FIG. 12 illustrates an exemplary logical flow diagram for calibrating a sleep apnea detection apparatus in accordance with some embodiments of the present disclosure.

FIG. 12 illustrates an exemplary logical flow diagram for calibrating the sleep apnea detection apparatus 100 in accordance with some embodiments of the disclosure. A routine 1200 begins at operation 1202, where the sleep apnea detection apparatus 100 is powered on. In various embodiments, the switch 136 may be configured to control the power being supplied to the sleep apnea detection apparatus 100. From operation 1202, the routine 1200 proceeds to operation 1204, where the microcontroller 202 determines whether the voltage being supplied by the power supply 132 is greater than a threshold voltage. If the microcontroller 202 determines that the voltage supplied by the power supply is not greater than the threshold voltage, the routine 1200 proceeds to operation 1206, where the microcontroller 202, via transducer 216, such as with a speaker, generates a stimulus indicating a low voltage. In various embodiments, the stimulus indicating a low voltage may be a signal having a specific frequency, amplitude and duration. For instance, the signal may be a 30 Hz signal that is generated for 2 seconds. In various embodiments, the threshold voltage may be set as a voltage that can provide power to the microcontroller 202, such that the microcontroller 202 can operate normally for a predetermined amount of time, for example, eight hours. It should be appreciated that the amount of power used by the microcontroller 202 may be based, in part on, how frequently the microcontroller 202 polls the dual-axis inclinometer 206 for pitch angle and roll angle information, as well as the frequency and duration for which stimuli are generated by the transducer 216.

From operation 1206, the routine 1200 proceeds back to operation 1202, where the sleep apnea detection circuit 200 is reset again. However, if, at operation 1204, the microcontroller 202 determines that the voltage being supplied by the power supply is greater than the threshold voltage, the routine 1200 proceeds to operation 1208, where the microcontroller 202 provides power to the dual-axis inclinometer 206. From operation 1208, the routine 1200 proceeds to operation 1210, where the microcontroller 202 receives, as an input, a pitch voltage corresponding to a pitch angle relative to the z-axis 310 and a roll voltage corresponding to a roll angle relative to the y-axis 308. It should be appreciated that the pitch voltage and roll voltage are merely examples of signals provided by the inclinometer 206.

From operation 1210, the routine 1200 proceeds to operation 1212, where the microcontroller 202 removes the power being supplied to the inclinometer 206. As part of polling the dual-axis inclinometer 206, the microcontroller supplies power to the dual-axis inclinometer 206, receives signals from the dual-axis inclinometer, and then removes power being supplied to the dual-axis inclinometer 206. In some embodiments, the microcontroller 202 may poll the dual-axis inclinometer 206 every twenty seconds. The microcontroller 202 supplies power to the dual-axis inclinometer for approximately 0.25 seconds, during which time the dual-axis inclinometer 206 is capable of generating signals corresponding to a current roll angle and pitch angle associated with the subject's head relative to the y-axis 308 and the z-axis 310, respectively. After 0.25 seconds, the microcontroller 202 stops supplying power to the dual-axis inclinometer 206, until after approximately 20 seconds, when the microcontroller 202 polls the dual-axis inclinometer 206 again. Since the microcontroller only supplies power to the dual-axis inclinometer 206 for approximately 1.2% (0.25 s/0.25 s) of the time that the apparatus 100 is operational, the battery life of the apparatus 100 is approximately 81 times better than any solution that requires the sensor, such as the dual-axis inclinometer 206, to be constantly powered on. For instance, using a sensor to detect a current position of the subject's head by detecting the movement of the subject's head requires the sensor to be constantly powered on. In contrast, by polling the dual-axis inclinometer 206 in the manner described herein can significantly improve battery life. It should be appreciated that the time between polling the dual-axis inclinometer 206 may be increased to further improve battery life. In alternate embodiments, the microcontroller 202 may continuously supply power to the dual-axis inclinometer 206, however, as explained above, a compromise on battery life.

From operation 1212, the routine 1200 proceeds to operation 1214, where the microcontroller 202 determines whether the signals from the inclinometer 206 representing the pitch angle and the roll angle lie within the range of values. In some embodiments, the microcontroller 202 determines whether the pitch voltage corresponds to a pitch angle that lies between approximately 170° and 190° relative to the z-axis 310, and whether the roll voltage corresponds to a roll angle that also lies between about 170° and 190° relative to the y-axis 308.

If, at operation 1214, the microcontroller 202 determines that either the pitch angle or the roll angle do not lie within the threshold values, the routine 1200 proceeds to operation 1216, where the microcontroller 202 may generate an alarm indicating that the sleep apnea detection apparatus 100 is not calibrated. From operation 1216, the routine 1200 proceeds to operation 1218, where the subject may adjust the orientation of the sleep apnea detection apparatus 100 within the subject's ear canal. In various embodiments, the adjustment may include rotating the sleep apnea detection apparatus 100 within the ear canal of the subject. Alternatively, during a one time planarity calibration, the adjustment may include rotating the sleep apnea detection circuit 200 within the interior chamber of the housing 110 by rotating the rotational component 138 of the sleep apnea detection apparatus 100. From operation 1218, the routine 1200 returns back to operation 1208, where the microcontroller 202 resumes the calibration process by providing power to the inclinometer 206.

If, at operation 1214, the microcontroller 202 determines that the pitch angle lies between approximately 170° and 190° relative to the z-axis 310 and the roll angle lies between approximately 170° and 190° relative to the y-axis 308, the routine 1200 proceeds from operation 1214 to operation 1220, where the microcontroller 202 may generate a stimulus indicating that the sleep apnea detection apparatus 100 has been calibrated. In various embodiments, the stimulus may be a signal, such as a 300 Hz signal that is generated for 3 seconds. From operation 1220, the routine 1200 proceeds to operation 1222, where the sleep apnea detection apparatus 100 may execute an apnea search algorithm, an embodiment of which is described with respect to FIG. 13.

Figure 13:
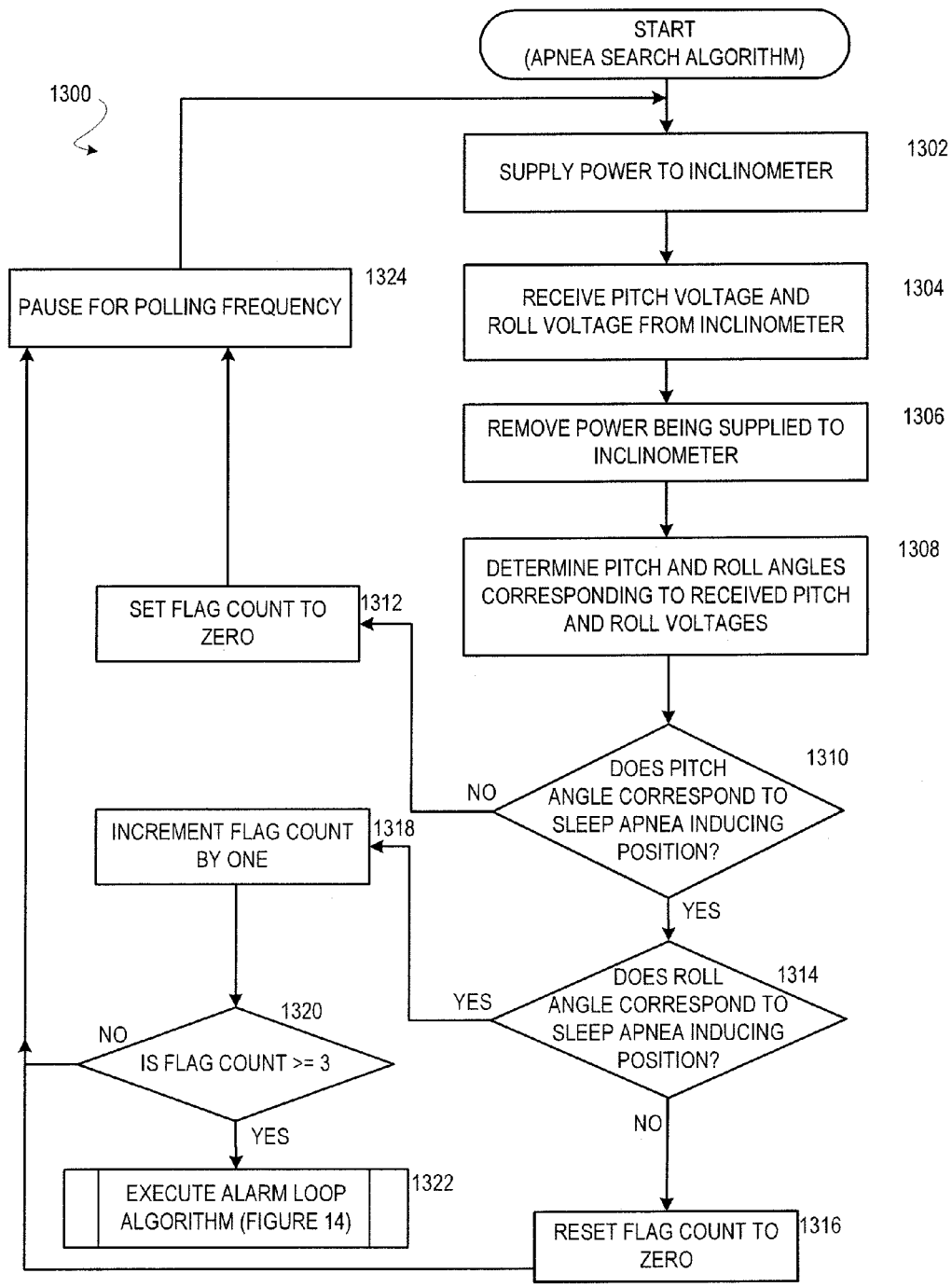
FIG. 13 illustrates an exemplary logical flow diagram for detecting whether the subject is in a sleep apnea inducing position in accordance with some embodiments of the present disclosure.

FIG. 13 illustrates an exemplary logical flow diagram associated with an apnea search algorithm configured to detect whether the subject is in a sleep apnea inducing position in accordance with some embodiments of the disclosure. A routine 1300 begins at operation 1302, where the microcontroller 202 provides power to the inclinometer 206. From operation 1302, the routine 1300 proceeds to operation 1304, where the inclinometer 206 generates a pitch voltage and a roll voltage corresponding to a pitch angle and a roll angle of a subject's head as explained previously. It should be appreciated that inclinometer 206 may generate any type of signal including but not limited to, a voltage, a current, a charge, etc. From operation 1304, the routine 1300 proceeds operation 1306, where the microcontroller 202 removes the power being supplied to the inclinometer 206. In various embodiments, the microcontroller 202 may provide and remove power being supplied to the inclinometer 206 in an effort to conserve energy and extend the battery life of the sleep apnea detection apparatus 100 as well as to minimize the number of false alarms, during repositioning.

From operation 1306, the routine 1300 proceeds to operation 1308, where the microcontroller 202 determines the pitch angle and the roll angle based on the signals received from the dual-axis inclinometer 206. From operation 1308, the routine 1300 proceeds to operation 1310, where the microcontroller 202 determines whether the pitch angle corresponds to a sleep apnea inducing pitch angle position. In various embodiments, the microcontroller 202 may determine that the pitch angle corresponds to a sleep apnea inducing pitch angle position if the pitch angle lies between approximately 20° and 160° relative to the z-axis 310. If, at operation 1310, the microcontroller 202 determines that the pitch angle does not correspond to a sleep apnea inducing pitch angle position, the routine 1300 proceeds to operation 1312, where the microcontroller 202 sets a flag count to zero. In various embodiments, a flag count may be a bit or a series of bits or any other data structure that may be used as a counter. From operation 1312, the routine 1300 proceeds to operation 1324, where the microcontroller 202 waits until the microcontroller 202 polls the dual-axis inclinometer 206 for new pitch and roll voltage readings.

However, if at operation 1310, the microcontroller 202 determines that the pitch angle corresponds to the sleep apnea inducing pitch angle position, the routine 1300 proceeds to operation 1314, where the microcontroller 202 determines whether the roll angle corresponds to a sleep apnea inducing roll angle position. In various embodiments, if the roll angle lies between approximately 25° and 155° relative to the y-axis 308, the subject is in a sleep apnea inducing position.

If, at operation 1314, the microcontroller 202 determines that the roll angle does not correspond to a sleep apnea inducing roll angle position, the routine 1300 proceeds to operation 1316, where the flag count is reset to zero. In this way, if the subject is no longer in a sleep apnea inducing position, a stimulus or alarm will not be activated. From operation 1316, the routine 1300 proceeds to operation 1324, where the microcontroller 202 waits until the microcontroller 202 polls the dual-axis inclinometer 206 for new pitch and roll voltage readings.

If, at operation 1314, the microcontroller 202 determines that the roll angle corresponds to a sleep apnea inducing roll angle position, the routine 1300 proceeds to operation 1318, where the microcontroller 202 increments the flag count by 1. From operation 1318, the routine 1300 proceeds to operation 1320, where the microcontroller 202 determines if the flag count is equal to or greater than an alarm generation threshold value. In some embodiments, the alarm generation threshold value may be set to 3. If, at operation 1320, the microcontroller 202 determines that the flag count is not equal to or greater than the alarm generation threshold value, the routine 1300 proceeds to operation 1324, where the microcontroller 202 waits until the microcontroller 202 polls the dual-axis inclinometer 206 for new pitch and roll voltage readings. However, if, at operation 1320, the microcontroller 202 determines that the flag count is equal to or greater than the alarm generation threshold value, the routine 1300 proceeds to operation 1322, where the microcontroller executes an alarm loop algorithm, which will be described with respect to FIG. 14.

Figure 14:
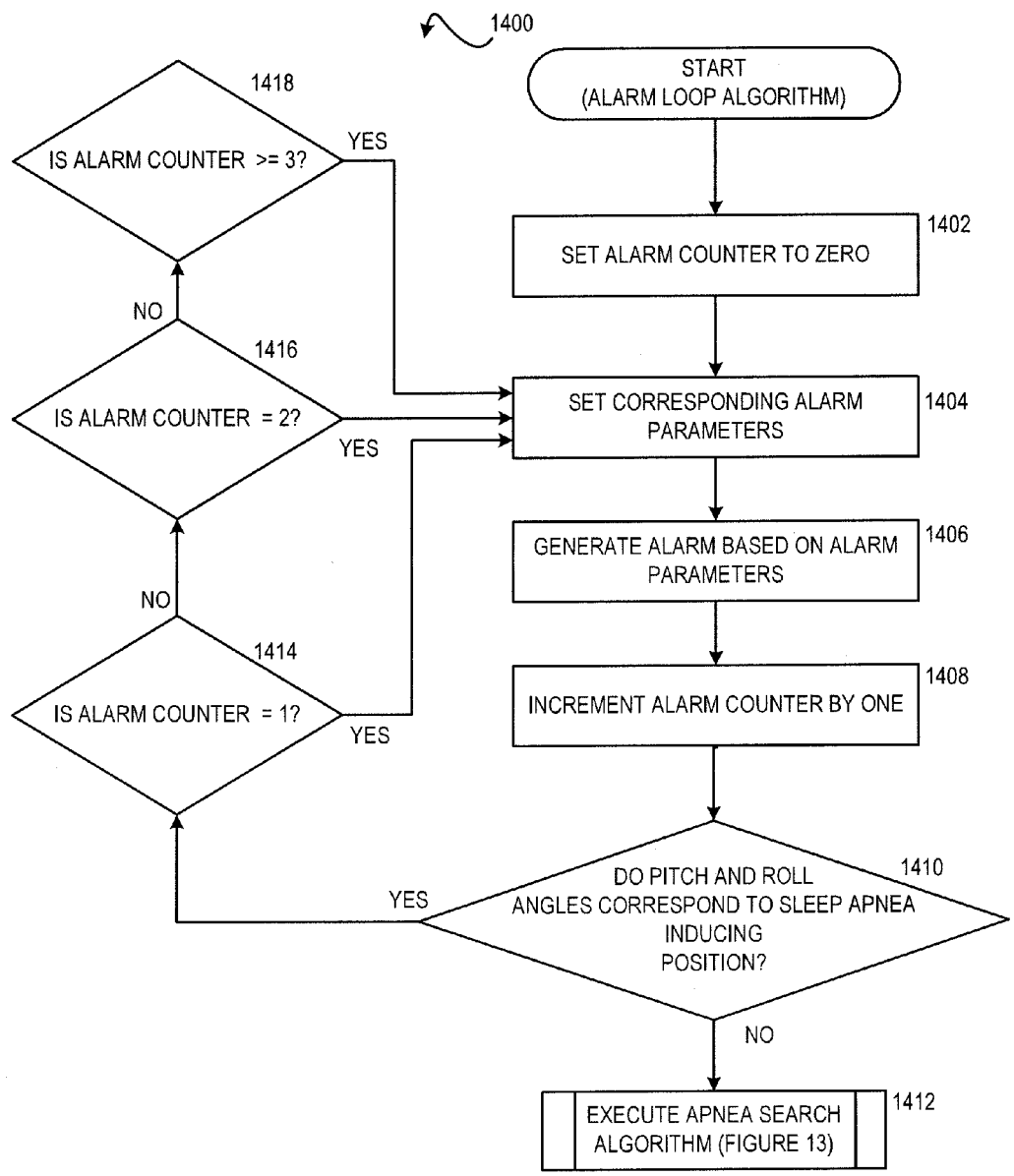
FIG. 14 illustrates an exemplary logical flow diagram for generating a stimulus in response to the subject's position in accordance with some embodiments of the present disclosure.

FIG. 14 illustrates an exemplary logical flow diagram for generating a stimulus if the subject is in a sleep apnea inducing position in accordance with some embodiments of the present disclosure. A routine 1400 begins at operation 1402, where the microcontroller 202 sets in an alarm counter to zero. From operation 1402, the routine 1400 proceeds to operation 1404, where the microcontroller 202 sets stimulus characteristics or parameters corresponding to the alarm counter being set to zero. From operation 1404, the routine 1400 proceeds to operation 1406, where the microcontroller 202 generates a stimulus. As described above, the stimulus may be a sound, a voice command, a vibration or other haptic stimulus, or any other notification that a subject is capable of sensing. It should be appreciated that the characteristics of any stimulus generated by the transducer 216 may include, but are not limited to, a frequency, an amplitude, and duration.

From operation 1406, the routine 1400 proceeds to operation 1408, where the microcontroller 202 increments the alarm counter by one. From operation 1408, the routine proceeds to operation 1410, where the microcontroller 202 determines if the pitch and roll angles correspond to the sleep apnea inducing positions. If, at operation 1410, the microcontroller 202 determines that the pitch and roll angles do not correspond to a sleep apnea inducing positions, the routine 1400 proceeds to operation 1412, where the microcontroller 202 executes the sleep apnea search algorithm, which is described herein with respect to FIG. 13. As described above, the microcontroller 202 may determine that the pitch and roll angles do not correspond to the sleep apnea inducing positions if either the pitch angle does not lie between approximately 20° and 160° relative to the z-axis 310, or if the roll angle does not lie between approximately 25° and 155° relative to the y-axis 308.

If, at operation 1410, the microcontroller 202 determines that the pitch angle and the roll angle correspond to a sleep apnea inducing position, the routine 1400 proceeds to operation 1414, where the microcontroller 202 determines if the alarm counter is equal to 1. If, at operation 1414, the microcontroller 202 determines that the alarm counter is equal to 1, the routine 1400 proceeds to operation 1404, where the microcontroller 202 sets alarm parameters corresponding to the alarm counter being equal to one. In various embodiments, the alarm parameters corresponding to the alarm counter being equal to 1 may be set to generate a gentle, audible signal, such as a signal having a frequency of approximately 30 Hz.

If, at operation 1414, the microcontroller 202 determines that the alarm counter is not equal to 1, the routine 1400 proceeds to operation 1416, where the microcontroller 202 determines if the alarm counter is equal to 2. If, at operation 1416, the microcontroller 202 determines that the flag count is equal to 2, the routine 1400 proceeds to operation 1404, where the microcontroller 202 sets alarm parameters corresponding to the alarm counter being equal to 2. In various embodiments, the alarm parameters corresponding to the alarm counter being equal to 2 may be set to generate a slightly more unpleasant audio signal, such as a signal having a frequency of approximately 100 Hz having a duration of 0.5 seconds.

If, at operation 1416, the microcontroller 202 determines that the alarm counter is not equal to 2, the routine 1400 proceeds to operation 1418, where the microcontroller 202 determines if the alarm counter is equal to or greater than 3. If, at operation 1416, the microcontroller 202 determines that the flag count is equal to or greater than 3, the routine 1400 proceeds to operation 1404, where the microcontroller 202 sets alarm parameters corresponding to the alarm counter being equal to or greater than 3. In various embodiments, the alarm parameters corresponding to the alarm counter being equal to 3 may be set to generate an even more unpleasant audio signal, such as a signal having a frequency of approximately 300 Hz for a duration of 0.5 seconds. As the alarm counter increases beyond 3, the alarm parameters may be set to generate a stimulus that is similar to an alarm clock. In one embodiment, the stimulus may have a frequency of approximately 300 Hz and may pulsate indefinitely with a duration of 1 second and gaps of 0.25 seconds. It should be appreciated that the alarm parameters associated with higher alarm counters may generate audible signals or other stimuli that are progressively more distracting than alarm parameters associated with lower alarm counters. For instance, the alarm parameters associated with an alarm counter of 3 may be louder, longer and have a different harmonic content than the alarm parameters associated with the alarm counter of 2 or the alarm counter of 1. It should be appreciated that the routine 1400 may end once the subject is no longer in a sleep apnea inducing position. In some embodiments, the microcontroller may be programmed to generate signals that correspond to a noise having particular characteristics or audio files having formats, including but not limited to, .mp3, .wav, .wma. Transducer 212 may also be implemented with a tactile for haptic stimulus generator, such as vibratoring mechanism which, when activated, creates a detectable vibrations, the parameters of which may be manipulated if the device is sequentially activated to create increasingly stronger stimulus until the subject reacts.

Figure 15:
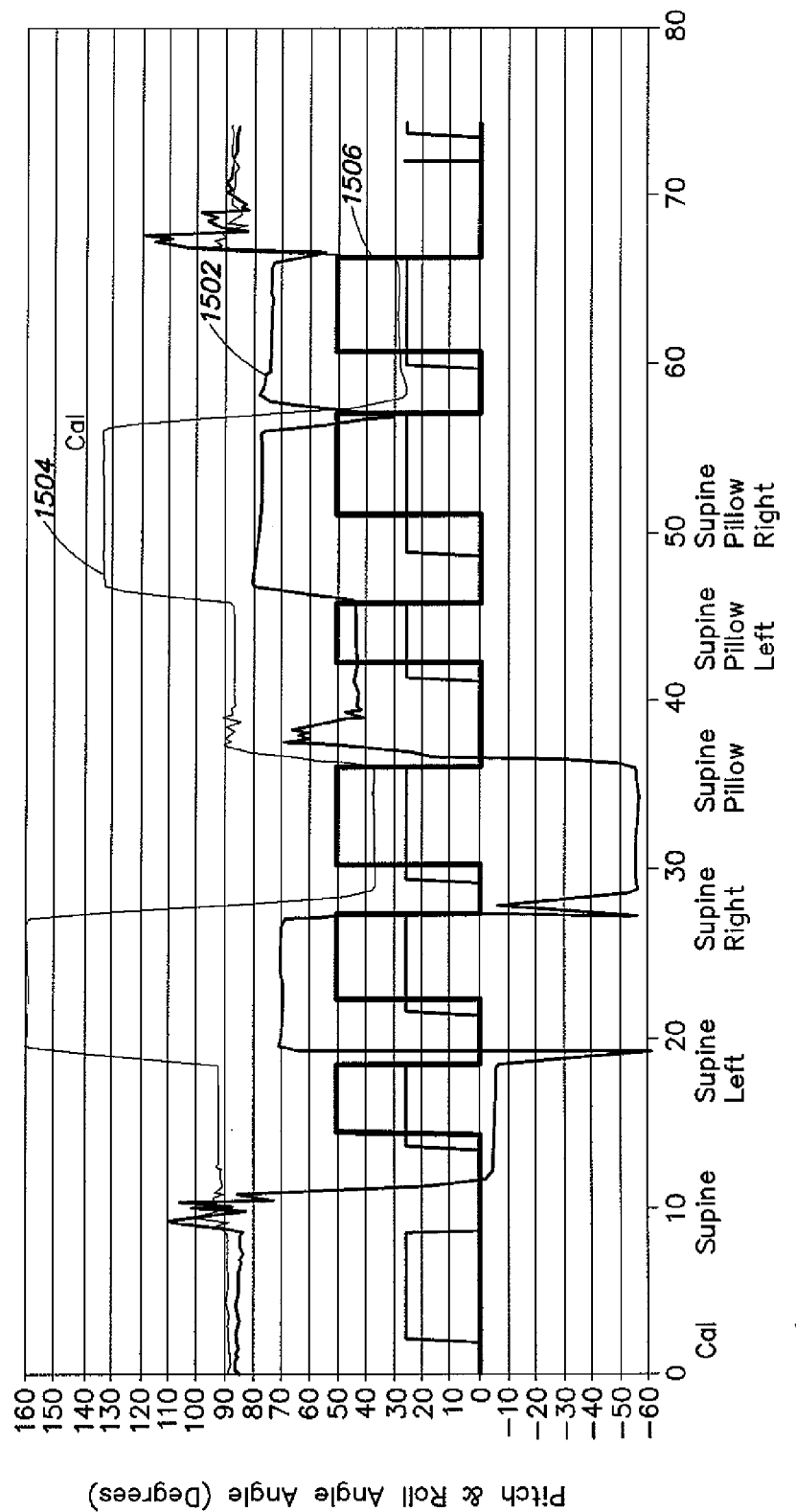
FIG. 15 illustrates a plot of various signals corresponding to the pitch angle, the roll angle, and an output signal generated by a microcontroller when the subject assumes supine positions that maximize the effects of apnea in accordance with some embodiments of the present disclosure.

Referring now to FIG. 15, a plot 1500 of various readings corresponding to the pitch angle, the roll angle, and an output signal generated by the microcontroller 202 when the subject assumes the six supine positions that maximize the effects of apnea is shown. The six supine positions that maximize the effects of apnea include 1) laying flat on back with no head elevation and face up; 2) laying flat on back with no head elevation and head turned as far as possible to the left; 3) laying flat on back with no head elevation and head turned as far as possible to the right; 4) laying flat on back with elevated head face up; 5) laying flat on back with elevated head and head turned as far as possible to the left; and 6) laying flat on back with elevated head and head turned as far as possible to the right. In various embodiments, the pitch angle formed by the elevated head is 115°. In particular, the plot 1500 shows a pitch signal 1502 that corresponds to the pitch angle of the subject's head relative to the horizontal axis 308, a roll signal 1504 that corresponds to the roll angle of the subject's head relative to the y-axis 308, and an output signal 1506 that corresponds to the generation of a stimulus when the subject's head is in a sleep apnea inducing position. As shown in the plot 1500, the output signal 1506 indicates that a stimulus was generated in each of the six supine positions that maximize the effects of apnea.

Figure 16:
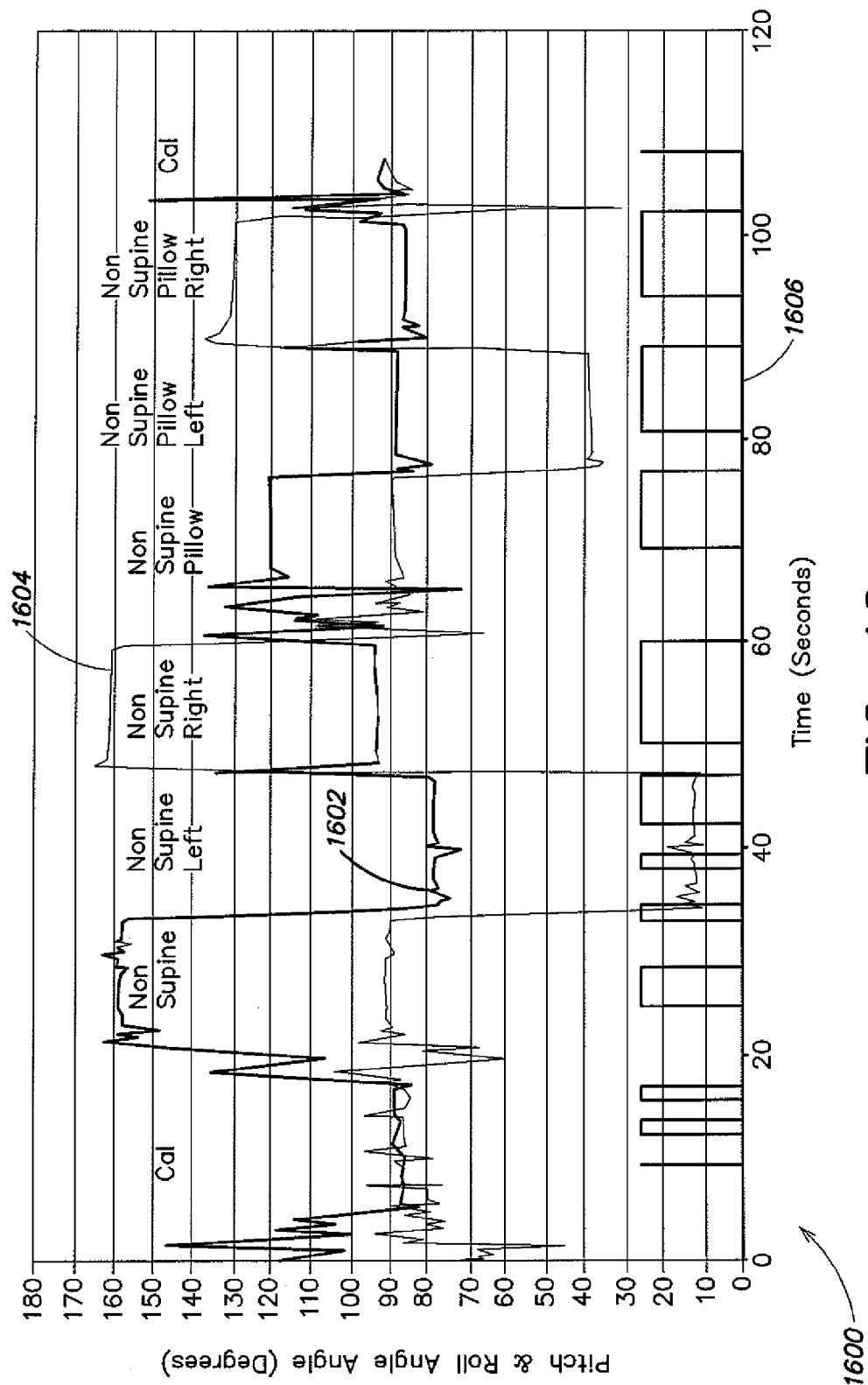
FIG. 16 illustrates a plot of various signals corresponding to the pitch angle, the roll angle, and an output signal generated by a microcontroller when the subject assumes non-supine positions that minimize the effects of apnea in accordance with some embodiments of the present disclosure.

Referring now to FIG. 16, a plot 1600 of various readings corresponding to the pitch angle, the roll angle, and an output signal generated by the microcontroller 202 when the subject assumes six non-supine positions that minimize the effects of apnea is shown. The six non-supine positions that minimize the effects of apnea include 1) laying flat on stomach with no head elevation and face down; 2) laying flat on stomach with no head elevation and head turned as far as possible to the left; 3) laying flat on stomach with no head elevation and with head turned as far as possible to the right; 4) laying flat on stomach with head elevation and face down; 5) laying flat on stomach with head elevation and head turned as far as possible to the left; and 6) laying flat on stomach with head elevation and head turned as far as possible to the right. In various embodiments, the pitch angle formed by the elevated head is 115°. In particular, the plot 1600 shows a pitch signal 1602 that corresponds to the pitch angle of the subject's head relative to the z-axis 310, a roll signal 1604 that corresponds to the roll angle of the subject's head relative to the y-axis 308, and an output signal 1606 that corresponds to the generation of a stimulus when the subject's head is in a sleep apnea inducing position. As shown in the plot 1600, the output signal 1606 indicates that no stimulus was generated in any of the six non-supine positions that minimize the effects of apnea.

Although the present disclosure provides methods for detecting sleep apnea, the disclosed system and technique should not be limited to specific implementations described herein. Rather, the present disclosure may relate to detecting other conditions, such as sleep walking, sudden infant death syndrome (SIDS), as well as an operator of a vehicle falling asleep. To implement the use of the sleep apnea detection apparatus in any of these conditions, the microcontroller may need to be programmed to determine when the pitch and roll angles associated with the subject's head corresponds to specific parameters associated with sleep walking, SIDS, or falling asleep during the operation of a vehicle. Note also that the sampling time of the algorithm may be optimized for each application.

In addition, the disclosed system and technique should not be restricted to any specific implementations here described, for which other beneficial or alternate implementations may be substituted, in order to satisfy the organizational, functional or technology requirements imposed upon this disclosed system by any implementer. It will be apparent to those skilled in the art that modifications to the specific embodiments described herein may be made while still being within the spirit and scope of the teachings disclosed herein.

What is claimed is:
1. A method for preventing sleep disorders comprising:
a) measuring, with a sensor, a pitch angle of a subject's head relative to an axis of gravity and a roll angle of the subject's head relative to a horizontal axis orthogonal to the axis of gravity;
b) modifying a flag count value with a controller while still monitoring the subject, if the subject's head is in a sleep apnea inducing position based on measurement data from the sensor and the flag count value is not equal to an alarm threshold value, else resetting the flag count value with said controller to an initial value while still monitoring the subject, if the subject's head is not in a sleep apnea inducing position based on the measurement data from the sensor;

c) repeating measuring step a) and modifying step b);

d) alerting the subject with stimulus from a transducer when the flag count value at least equals the alarm threshold value; and e) setting the flag count value with said controller to the initial value which is different from the alarm threshold value by commencement of monitoring of the subject;

wherein a sleep apnea inducing position is defined as the subject's head having a measured pitch angle of between approximately 20° and 160° relative to the axis of gravity and a measured roll angle of between approximately 25° and 155° relative to the horizontal axis orthogonal to the axis of gravity.

2. The method of claim 1 wherein alerting step d) comprises:
   d1) generating one of an audio and haptic stimulus detectable by the subject.

3. The method of claim 1 wherein the flag count value represents the number of consecutive times the subject's head is in a sleep apnea inducing position based on measurements from the sensor while monitoring the subject.

4. The method of claim 1 wherein measuring step a) comprises:
   a1) comparing a measured pitch angle to a predefined range of threshold pitch angles.

5. The method of claim 4 wherein modifying step b) comprises:
   b1) modifying the flag count value if the measured pitch angle lies within the predefined range of threshold pitch angles.

6. The method of claim 5 wherein modifying step b1) comprises:
   b1a) one of incrementing and decrementing the flag count value while still monitoring the subject, if the measured pitch angle lies within the predefined range of threshold pitch angles; and
   b1b) else resetting the flag count value to the initial value, while still monitoring the subject, if the measured pitch angle is not within the predefined range of threshold pitch angles.

7. The method of claim 1 wherein measuring step a) comprises:
   a1) comparing a measured roll angle to a predefined range of threshold roll angles.

8. The method of claim 7 wherein modifying step b) comprises:
   b1) modifying the flag count value if the measured roll angle lies within the predefined range of threshold roll angles.

9. The method of claim 8 wherein modifying step b1) comprises:
   b1a) one of incrementing and decrementing the flag count value while still monitoring the subject, if the measured roll angle lies within the predefined range of threshold roll angles; and
   b1b) else resetting the flag count value to the initial value, while still monitoring the subject, if the measured roll angle is not within the predefined range of threshold roll angles.

10. A method of monitoring a subject to prevent sleep disorders, the method comprising the steps of:
   a) measuring, with a sensor, a pitch angle of a subject's head relative to an axis of gravity;
   b) comparing, with a controller, the measured pitch angle to a predetermined range of pitch angles that correspond to sleep apnea inducing positions;
   c) measuring, with a sensor, a roll angle of a subject's head relative to a horizontal axis orthogonal to the axis of gravity;
   d) comparing, with said controller, the measured roll angle to a predetermined range of roll angles that correspond to sleep apnea inducing positions;
   e) modifying, with a controller, a flag count value if the measured roll angle is within the predetermined range of roll angles and the measured pitch angle is within the predetermined range of roll angles indicating that the subject's head is in a sleep apnea inducing position and the flag count value is not equal to an alarm threshold value,
   else re-setting, with said controller, the flag count value to a predetermined value if the subject's head is not within the predetermined range of pitch and roll angles corresponding to a sleep apnea inducing position;
   f) repeating steps a) through e) if the flag count value is not equal to the predetermined alarm threshold value; and
   g) alerting, with a transducer, the subject with stimulus when the flag count value at least equals the predetermined alarm threshold value;
   wherein a sleep apnea inducing position is defined as the subject's head having a measured pitch angle of between approximately 20° and 160° relative to the axis of gravity and a measured roll angle of between approximately 25° and 155° relative to the horizontal axis orthogonal to the axis of gravity.

* * * * *